(12) United States Patent
Blackburn

(10) Patent No.: US 7,642,281 B2
(45) Date of Patent: Jan. 5, 2010

(54) INDOLONE COMPOUNDS USEFUL TO TREAT COGNITIVE IMPAIRMENT

(75) Inventor: Thomas P. Blackburn, Hoboken, NJ (US)

(73) Assignee: Helicon Therapeutics, Inc., San Diego, CA (US)

( * ) Notice: Subject to any disclaimer, the term of this patent is extended or adjusted under 35 U.S.C. 154(b) by 340 days.

(21) Appl. No.: 11/608,746

(22) Filed: Dec. 8, 2006

(65) Prior Publication Data

US 2007/0135510 A1    Jun. 14, 2007

Related U.S. Application Data

(63) Continuation-in-part of application No. 10/637,299, filed on Aug. 7, 2003, now Pat. No. 7,220,775.

(60) Provisional application No. 60/748,851, filed on Dec. 9, 2005, provisional application No. 60/402,035, filed on Aug. 7, 2002.

(51) Int. Cl.
*A61K 31/4015*    (2006.01)
*A61K 31/404*    (2006.01)
*C07D 209/34*    (2006.01)

(52) U.S. Cl. .................. 514/414; 514/418; 548/467; 548/483

(58) Field of Classification Search .................. None
See application file for complete search history.

(56) References Cited

U.S. PATENT DOCUMENTS 5,576,296 A * 11/1996 Bartfai et al. .................. 514/13
6,329,197 B2 * 12/2001 Bard et al. .................. 435/320.1
7,064,181 B1 * 6/2006 Ohtaki et al. .................. 530/350
7,081,470 B2 * 7/2006 Konkel et al. .................. 514/411

FOREIGN PATENT DOCUMENTS

| EP | 0629615 A1 | 12/1994 | .................. 209/40 |
| WO | WO 2004/014307 A2 | 2/2004 | |
| WO | WO 2004/014376 A | 2/2004 | .................. 31/44 |
| WO | WO 2004/014854 A | 2/2004 | .................. 209/2 |

OTHER PUBLICATIONS

McDonald et al., "Galanin Inhibits Performance on Rodent Memory Tasks" Annals of the New York Academy of Sciences (1998) vol. 863, pp. 305-322.*

Mufson Elliott, J. et al., "Galanin expression within the basal forebrain in Alzheimer's disease: Comments on therapeutic potential", Annals of the New York Academy of Sciences; Galanin: Basic research discoveries and therapeutic implications , pp. 209-304, 1998.

Konkel, Michael J. et al., "3-Arylimino-2-indolones are potent and selective Galanin GAL3 receptor Antagonists", Journal of Medicinal Chemistry, pp. 3757-3758, 2006.

Mitsukawa, K. et al., "Galanin, galanin receptors and drug targets", Cell. Mol. Life Sci. 65 (2008) 1796-1805.

* cited by examiner

*Primary Examiner*—Shaojia Anna Jiang
*Assistant Examiner*—Eric S Olson
(74) *Attorney, Agent, or Firm*—Sheppard, Mullin, Richter & Hampton LLP

(57) ABSTRACT

This invention provides a method of treating a subject suffering from a cognitive impairment or a cognitive disorder which comprises administering to the subject an amount of an indolone compound effective to treat the subject's cognitive impairment or disorder.

12 Claims, 3 Drawing Sheets

INDOLONE COMPOUNDS USEFUL TO TREAT COGNITIVE IMPAIRMENT

CROSS-REFERENCE TO RELATED APPLICATIONS

This is a non-provisional application tiled under 37 C.F.R. §1.53(b), claiming priority under 35 U.S.C. §119(e) to provisional Application Ser. No. 60/748,851, filed Dec. 9, 2005 which is incorporated by reference herein, and claiming priority under 35 U.S.C. §120 as a Continuation-in-Part of U.S. application Ser. No. 10/637,299 filed Aug. 7, 2003 now U.S. Pat. No. 7,220,775, which claims priority to provisional Application Ser. No. 60/402,035 filed Aug. 7, 2002.

BACKGROUND OF INVENTION

An estimated four to five million Americans (about 2% of all ages and 15% of those older than 65) have some form and degree of cognitive impairment. Cognitive impairment or reduction of cognitive functions commonly occurs in association with central nervous system (CNS) disorders or conditions.

Cognition generally refers to the process by which knowledge is acquired, retained and used by subjects. Both memory and thinking are involved in the storage, retrieval, and manipulation of information. Cognitive disorders are abnormalities of thinking and memory that are associated with temporary or permanent brain dysfunction. Their main symptoms include problems with memory, orientation, language, information processing, and the ability to focus and sustain attention on a task. Examples of CNS disorders or conditions that fall within the scope of the present invention include, but are not limited to, age-associated memory impairment (AAMI); mild cognitive impairment (MCI); delirium (aka acute confusional state); dementia (sometimes further classified as Alzheimer's or non-Alzheimer's type dementia); Alzheimer's disease; Parkinson's disease; Huntington's disease (aka chorea); mental retardation; (e.g., Rubenstein-Taybi and Downs Syndrome); cerebrovascular disease (e.g., vascular dementia, post-cardiac surgery); affective disorders; psychotic disorders; autism (aka Kanner's Syndrome); neurotic disorders; attention deficit disorder (ADD); subdural hematoma; normal-pressure hydrocephalus; brain tumor; head trauma (postconcussional disorder) and brain trauma (see DSM-FV, APA 1994). Amnestic and cognitive disorders with or without an established cause are described in DSM-UV. Other cognitive disorders specified in DSM-IV, include learning, motor skills and communication skills disorders (DSM-IV 315.00-315.39). For the purposes of the present invention the terms cognitive impairment and cognitive disorder are deemed to cover the same therapeutic indications. Accordingly, the terms cognitive impairment and cognitive disorder are used interchangeably throughout this application.

Cognitive impairment is typically manifested by one or more cognitive deficits. Memory impairment is a cognitive deficit characterized by the inability to learn new information or to recall previously learned information. Aphasia is a cognitive deficit characterized by a language and/or speech disturbance. Apraxia is a cognitive deficit characterized by the impaired ability to carry out motor activities despite intact motor function according to DSM-UV. Agnosia is a cognitive deficit characterized by the failure to recognize or identify objects despite intact sensory function (as described in DSM-UV). Cognitive impairment may also be manifested by a disturbance in executive functioning (i.e., planning, organizing, sequencing, abstracting). The present invention is directed to a method of treating a subject suffering from a cognitive impairment or a cognitive disorder wherein the cognitive impairment or cognitive disorder is manifested by one or more of the cognitive deficits described herein.

Cognitive impairment or reduction of cognitive function causes significant impairment of social and/or occupational functioning which can interfere with the ability of an individual to perform activities of daily living and greatly impact the autonomy and quality of life of the individual.

Consequently, there is a need for therapies to treat cognitive disorders and cognitive impairments. The indolone compounds of the present invention have now been found to show potent effects in models of cognitive impairment, thereby filling this void in the current state of the art. Applicants further note that the indolone compounds described herein have been previously characterized as GALR3 receptor antagonists (see WO 02/060392), thereby supporting the broader theory that GALR3 receptor antagonists may be useful to treat cognitive disorders.

SUMMARY OF THE INVENTION

The present invention provides a method of treating a subject suffering from a cognitive impairment which comprises administering to the subject an amount of compound effective to treat the subject's cognitive impairment, wherein the compound has the structure:

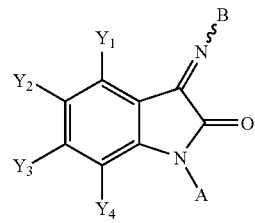

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl($C_1$-$C_6$)alkyl;

wherein A' is

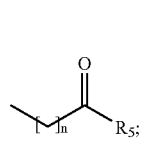 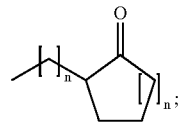

wherein $R_1$ and $R_2$ are each independently —H, straight chained or branched $C_1$-$C_7$ alkyl, —

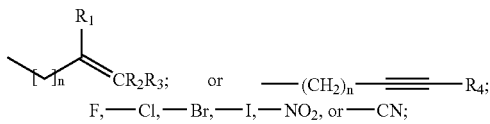

wherein $R_3$ is —H, straight chained or branched $C_1$-$C_7$ alkyl, —F, —Cl, —Br, —I, —NO$_2$, CN, —OR$_6$, aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following: —H, —F, —Cl, —Br, —I, —CN, methyl, ethyl or methoxy;

wherein each n is independently an integer from 1 to 4 inclusive;

wherein the compound is a pure Z imine isomer, a pure E imine isomer, or a mixture of Z and E imine isomers;

or a pharmaceutically acceptable salt thereof.

The indolone compounds of the present invention may be utilized to treat any of the cognitive impairments and/or cognitive disorders described herein.

DETAILED DESCRIPTION OF THE INVENTION

Figure 1:
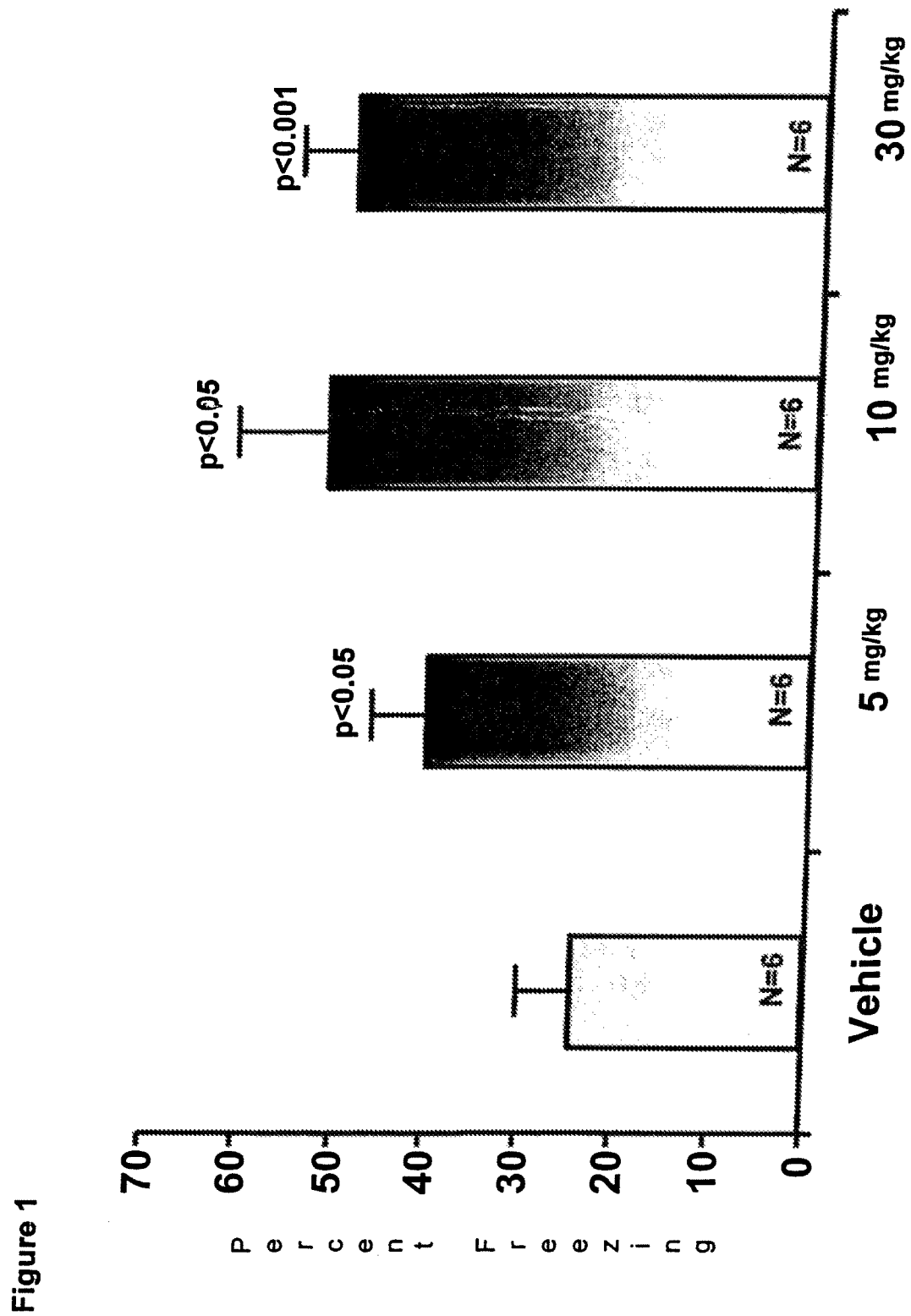
FIG. 1: Effects of Compound 2 on contextual memory in mice. 5 mg/kg, 10 mg/kg and 30 mg/kg of Compound 2 significantly facilitated freezing to context 24 hours after training. All dosages of vehicle and Compound 2 were administered intraperitonially (i.p.).

The present invention provides a method of treating a subject suffering from a cognitive impairment which comprises administering to the subject an amount of compound effective to treat the subject's cognitive impairment wherein the compound has the structure:

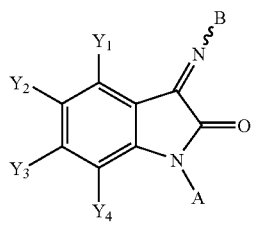

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —NO$_2$; —N$_3$; —CN; —OR$_4$, —SR$_4$, —OCOR$_4$, —COR$_4$, —NCOR$_4$, —N(R$_4$)$_2$, —CON(R$_4$)$_2$, or —COOR$_4$; aryl or heteroaryl; or any two of $Y_1$, $Y_2$, $Y_3$ and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl($C_1$-$C_6$)alkyl;

wherein A' is

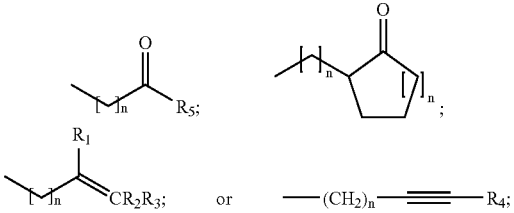

wherein $R_1$ and $R_2$ are each independently H, straight chained or branched $C_1$-$C_7$ alkyl, —F, —Cl, —Br, —I, —NO$_2$, or —CN;

wherein $R_3$ is H, straight chained or branched $C_1$-$C_7$ alkyl, —F, —Cl, —Br, —I, —NO$_2$, —CN, —OR$_6$, aryl or heteroaryl;

wherein $R_5$ is straight chained or branched $C_1$-$C_7$ alkyl, —N(R$_4$)$_2$, —OR$_6$ or aryl;

wherein $R_6$ is straight chained or branched $C_1$-$C_7$ alkyl or aryl;

wherein B is aryl, or heteroaryl; provided however, if B is aryl or heteroaryl the carbon atom or carbon atoms ortho to the nitrogen atom of the imine bond may only be substituted with one or more of the following: —H, —F, —Cl, —Br, —I, —CN, methyl, ethyl or methoxy;

wherein each n is independently an integer from 1 to 4 inclusive;

wherein the compound is a pure Z imine isomer, a pure E imine isomer, or a mixture of Z and E imine isomers;

or a pharmaceutically acceptable salt thereof.

In the present invention, the term "straight chained or branched $C_1$-$C_7$ alkyl" refers to a saturated hydrocarbon moiety having from one to seven carbon atoms inclusive. Examples of such substituents include, but are not limited to, methyl, ethyl, 1-propyl, 2-propyl, 1-butyl, 2-butyl, 2-methyl-2-propyl and 2-methyl-1-propyl. The term "$C_2$-$C_7$ alkenyl" refers to a mono-unsaturated hydrocarbon moiety having from two to seven carbon atoms inclusive. Examples of such substituents include, but are not limited to, ethenyl, prop-1-en-1-yl, prop-1-en-2-yl, prop-2-en-1-yl, but-3-en-2-yl and hept-2-en-1-yl. The term "$C_3$-$C_7$ alkynyl" refers to a hydrocarbon moiety having from three to seven carbon atoms and containing one carbon-carbon triple bond. Examples of such substituents include, but are not limited to, prop-1-ynyl, prop-2-ynyl, pent-2-ynyl, 4,4-dimethylpent-2-ynyl, 5-methylhex-3-yn-2-yl and hept-3-ynyl.

As used in the present invention, the term "cycloalkyl" includes $C_3$-$C_7$ cycloalkyl moieties which may be substituted with one or more of the following: —F, —NO$_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$, wherein each m is independently an integer from 0 to 2 inclusive.

As used in the present invention, the term "cycloalkenyl" includes $C_5$-$C_7$ cycloalkenyl moieties which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$, wherein each m is independently an integer from 0 to 2 inclusive.

In the present invention, the term "heteroaryl" is used to include five and six membered unsaturated rings that may contain one or more oxygen, sulfur, or nitrogen atoms. Examples of heteroaryl groups include, but are not limited to, furanyl, thienyl, pyrrolyl, oxazolyl, thiazolyl, imidazolyl, pyrazolyl, isoxazolyl, isothiazolyl, oxadiazolyl, triazolyl, thiadiazolyl, pyridyl, pyridazinyl, pyrimidinyl, pyrazinyl, and triazinyl.

In addition the term "heteroaryl" is used to include fused bicyclic ring systems that may contain one or more heteroatoms such as oxygen, sulfur and nitrogen. Examples of such heteroaryl groups include, but are not limited to, indolizinyl, indolyl, isoindolyl, benzo[b]furanyl, benzo[b]thiophenyl, indazolyl, benzimidazolyl, purinyl, benzoxazolyl, benzisoxazolyl, benzo[b]thiazolyl, imidazo[2,1-b]thiazolyl, cinnolinyl, quinazolinyl, quinoxalinyl, 1,8-naphthyridinyl, pteridinyl, quinolinyl, isoquinolinyl, phthalimidyl and 2,1,3-benzothiazolyl.

The term "heteroaryl" also includes those chemical moieties recited above which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$COR_4$, —$NCOR_4$, —$CO_2R_4$, —$CON(R_4)_2$ or $(CH_2)_n$—O—$(CH_2)_m$—$CH_3$, wherein each m is independently an integer from 0 to 2 inclusive.

The term "heteroaryl" further includes the N-oxides of those chemical moieties recited above which include at least one nitrogen atom.

In the present invention the term "aryl" is phenyl or naphthyl. The term "aryl" also includes phenyl and naphthyl which may be substituted with one or more of the following: —F, —Cl, —Br, —I, —$NO_2$, —CN, straight chained or branched $C_1$-$C_7$ alkyl, straight chained or branched $C_1$-$C_7$ monofluoroalkyl, straight chained or branched $C_1$-$C_7$ polyfluoroalkyl, straight chained or branched $C_2$-$C_7$ alkenyl, straight chained or branched $C_2$-$C_7$ alkynyl, $C_3$-$C_7$ cycloalkyl, $C_3$-$C_7$ monofluorocycloalkyl, $C_3$-$C_7$ polyfluorocycloalkyl, $C_5$-$C_7$ cycloalkenyl, —$N(R_4)_2$, —$OR_4$, —$SR_4$, —$OCOR_4$, —$COR_4$, —$NCOR_4$, —$CO_2R_4$, $CON(R_4)_2$ or $(CH_2)_n$—O—$(CH_2)_m$—$CH_3$, wherein each m is independently an integer from 0 to 2 inclusive.

The present invention also provides a method of treating a subject suffering from a cognitive impairment which compromises administering to the subject an amount of compound effective to treat the subject's cognitive impairment, wherein the compound has the structure:

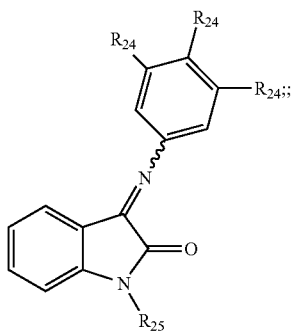

wherein each $R_{24}$ is independently one or more of the following: H, F, Cl, Br, I, $CF_3$ or $OCH_3$;

wherein $R_{25}$ is methyl, ethyl, allyl or phenyl and the phenyl is optionally substituted with a F, Cl, Br, $CF_3$, or $OR_4$; and wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl.

In the methods described herein, the compound contains an imine bond, which can potentially have a Z or E stereoconfiguration. In one embodiment of any of the methods described herein, the compound is a pure Z imine isomer. In one embodiment of any of the methods described herein, the compound is a pure E imine isomer. In one embodiment of any of the methods described herein, the compound is a mixture of Z and E imine isomers.

In the methods described herein, the compound may contain an alkene bond, which can potentially have a Z or E stereoconfiguration. For example, the compound may contain a group $Y_2$ attached to the 5-position of an indolone ring system, where $Y_2$ is but-2-en-1-yl. Such a butenyl group can potentially have a Z or E stereoconfiguration. In one embodiment of any of the methods described herein, the compound is a pure Z alkene isomer. In one embodiment of any of the methods described herein, the compound is a pure E alkene isomer. In one embodiment of any of the methods described herein, the compound is a mixture of Z and E alkene isomers.

In the methods described herein, the compound may contain one or more moieties that are capable of chirality. Such moieties may include, but are not limited to, quadrivalent chiral atoms or ring systems with restricted rotation giving rise to perpendicular dissymmetric planes. In one embodiment of any of the methods described herein, the compound is enantiomerically or diastereomerically pure. In one embodiment of any of the methods described herein, the compound is enantiomerically and diastereomerically pure. In one embodiment of any of the methods described herein, the compound is a mixture of enantiomers. In one embodiment of any of the methods described herein, the compound is a mixture of diastereomers.

In one embodiment, the compound is administered orally.
In one embodiment, the compound has the structure:

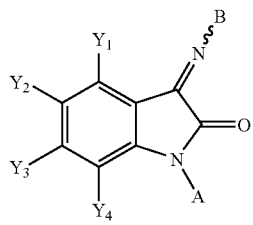

wherein each of $Y_1$, $Y_2$, $Y_3$, and $Y_4$ is independently —H; straight chained or branched $C_1$-$C_7$ alkyl, —$CF_3$, —F, —Cl, —Br, —I, —$OR_4$, —$N(R_4)_2$, or —$CON(R_4)_2$;

wherein each $R_4$ is independently —H; straight chained or branched $C_1$-$C_7$ alkyl, —$CF_3$, or phenyl;

wherein A is A', straight chained or branched $C_1$-$C_7$ alkyl, aryl, heteroaryl, aryl($C_1$-$C_6$)alkyl or heteroaryl($C_1$-$C_6$)alkyl; and wherein A' is

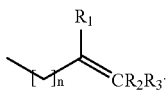

In one embodiment, B is heteroaryl. In another embodiment, B is aryl.

In one embodiment, B is phenyl and the phenyl is optionally substituted with one or more of the following: —H, —F, —Cl, —Br, —$CF_3$, straight chained or branched $C_1$-$C_7$ alkyl, —$N(R_4)_2$, —$OR_4$, —$COR_4$, —$NCOR_4$, —$CO_2R_4$, or —$CON(R_4)_2$.

In one embodiment, A is aryl. In another embodiment, A is heteroaryl.

In one embodiment, the compound is selected from the group consisting of:

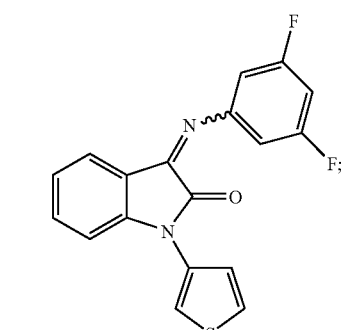

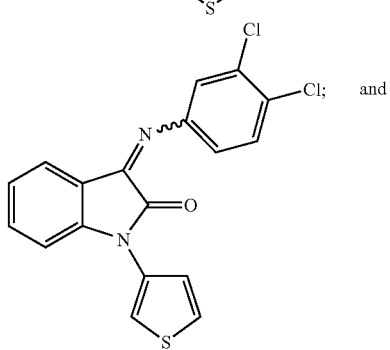

and

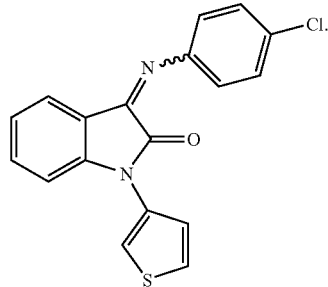

In one embodiment, the compound is selected from the group consisting of:

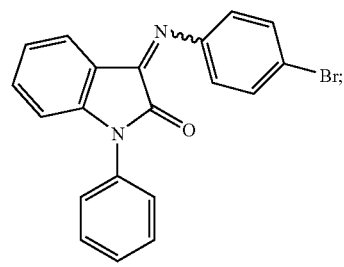

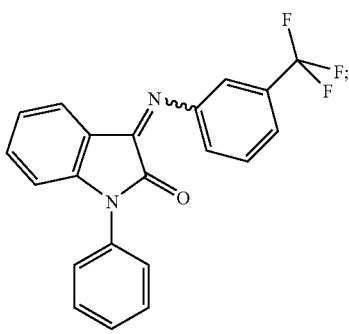

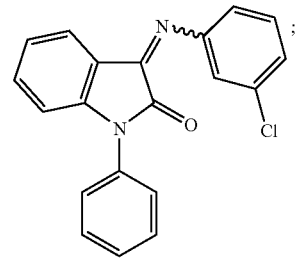

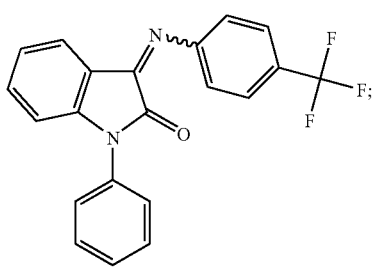

-continued

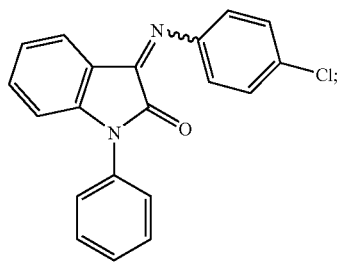

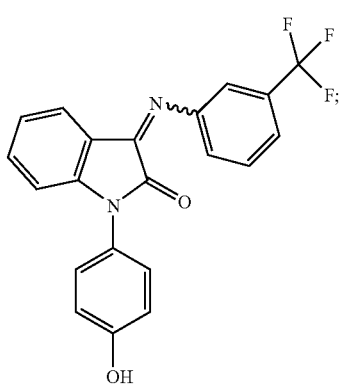

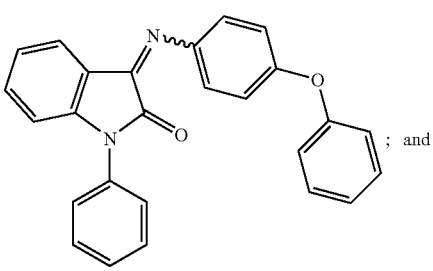

In one embodiment, A is A' and A' is

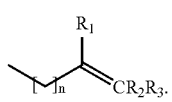

In one embodiment, the compound is:

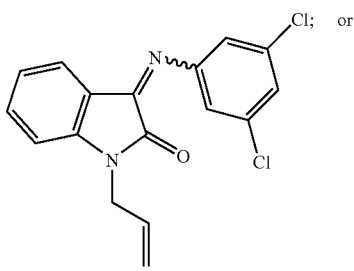

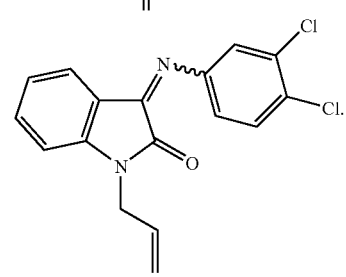

In one embodiment, A is aryl. In another embodiment, B is aryl.

In one embodiment, A is heteroaryl($C_1$-$C_6$)alkyl.

In one embodiment, the compound is:

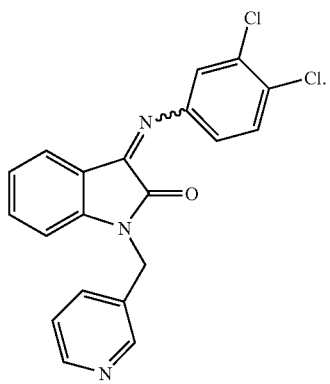

The invention provides a method of treating a subject suffering from a cognitive impairment which comprises administering to the subject an amount of any of the compounds described herein effective to treat the subject's cognitive impairment.

As previously discussed, cognitive disorders are abnormalities of thinking and memory that are associated with temporary or permanent brain dysfunction. The claimed invention is directed to methods of treating cognitive disorders and cognitive impairments which comprises administering therapeutically effective amounts of the indolone compounds described herein.

Examples of CNS disorders or conditions that fall within the scope of the present invention include, but are not limited to, age-associated memory impairment (AAMI); mild cognitive impairment (MCI), delirium (aka acute confusional state); dementia (sometimes further classified as Alzheimer's or non-Alzheimer's type dementia); Alzheimer's disease; Parkinson's disease; Huntington's disease (aka chorea); mental retardation; (e.g., Rubenstein-Taybi and Downs Syndrome); cerebrovascular disease (e.g., vascular dementia, post-cardiac surgery); affective disorders; psychotic disorders; autism (aka Kanner's Syndrome); neurotic disorders; attention deficit disorder (ADD); subdural hematoma; normal-pressure hydrocephalus; brain tumor; head trauma (post-concussional disorder) and brain trauma (see DSM-IV, APA 1994). The main symptoms of cognitive disorders and cognitive impairments include problems with memory, orientation, language, information processing, and the ability to focus and sustain attention on a task. Accordingly, any disease, disorder or condition which symptoms include problems associated with memory, orientation, language, information processing and/or the ability focus and sustain attention on a task may be treated by administering a therapeutically effective amount of the indolone compounds described herein.

In one embodiment of the present invention, the cognitive impairment is associated with a psychiatric disorder, a psychotic disorder, a neurological disorder or a neurotic disorder. In a specific embodiment, the psychotic disorder is schizophrenia. In a further embodiment, the cognitive impairment is associated with a disorder of the central nervous system. In yet another embodiment, the disorder of the central nervous system is age-associated memory impairment, mild cognitive impairment, Alzheimer's disease or Parkinson's disease. The present invention also covers methods of treating cognitive impairments wherein the cognitive impairment is associated with head trauma, brain trauma or cerebrovascular disease. In a specific embodiment, the cerebrovascular disease is vascular dementia. The present invention also covers methods of treating cognitive impairments wherein the cognitive impairment is associated with an affective disorder.

Synthesis of Chemical Compounds

The following description illustrates methods that may be used to synthesize the indolone compounds of this invention.

General Methods

All reactions were performed under an Argon atmosphere and the reagents, neat or in appropriate solvents, were transferred to the reaction vessel via syringe and cannula techniques. Anhydrous solvents were purchased from the Aldrich Chemical Company and used as received. The compounds described below were named using the ACD/Name Program (version 4.01, Advanced Chemistry Development Inc., Toronto, Ontario, M5H2L3, Canada). The $^1$H NMR and $^{13}$C NMR spectra were recorded at either 300 MHz (GEQE Plus) or 400 MHz (Bruker Avance) in CDCl$_3$ as solvent and tetramethylsilane as the internal standard unless otherwise noted. Chemical shifts (δ) are expressed in ppm, coupling constants (J) are expressed in Hz, and splitting patterns are described as follows: s=singlet; d=doublet; t=triplet; q=quartet; quintet; sextet; septet; br=broad; m=mutiplet; dd=doublet of doublets; dt=doublet of triplets. Elemental analyses were performed by Robertson Microlit Laboratories, Inc. Unless indicated otherwise, mass spectra were obtained using electrospray ionization (ESI, Micromass Platform II) and MH$^+$ is reported. Thin-layer Chromatography (TLC) was carried out on glass plates pre-coated with silica gel 60 F$_{254}$ (0.25 mm, EM Separations Tech.). Preparative TLC was carried out on glass sheets pre-coated with silica gel GF (2 mm, Analtech). Flash column chromatography was performed on Merck silica gel 60 (230-400 mesh). Melting points (mp) were determined in open capillary tubes on a Mel-Temp apparatus and are uncorrected.

The following additional abbreviations are used: HOAc, acetic acid; DIPEA, diisopropylethylamine; DMF, N,N-dimethylformamide; EtOAc, ethyl acetate; MeOH, methanol; TEA, triethylamine; THF, tetrahydrofuran; All solvent ratios are volume/volume unless stated otherwise.

I. General Procedure for Preparing Indolones

The methods that follow demonstrate procedures useful for synthesizing compounds of this invention (illustrated in Schemes 1-5). Substituted isatins useful for synthesizing compounds of this invention can alternatively be obtained using the procedures described in the following references:

Garden, S. J.; Da Silva, L. E.; Pinto, A. C.; *Synthetic Communications*, 1998, 28, 1679-1689.

Coppola, G. M.; *Journal of Heterocyclic Chemistry*, 1987, 24, 1249.

Hess, B. A. Jr; Corbino, S.; *Journal of Heterocyclic Chemistry*, 1971, 8, 161.

Bryant, W. M. III; Huhn, G. F.; Jensen, J. H.; Pierce, M. E.; Stammbach, C.; *Synthetic Communications*, 1993, 23, 1617-1625.

General Procedure for Synthesis of Iminoisatins

The appropriately substituted isatin (10 mg-10 g) was placed in a flask and the appropriate aniline (1.0-1.1 equivalents) was added and the mixture was stirred to homogeneity. The mixture was then heated to 110° C. for 2-7 hours and then cooled. Solids were crystallized from hot methanol and filtered, giving the desired products (usually as an inseparable interconverting mixture of E/Z isomers).

Procedure A:

1-(3-THIENYL)-1H-INDOLE-2,3-DIONE: Triethylamine (56.9 mL, 0.408 mol), was added to a mixture of 1H-indole-2,3-dione (15.0 g, 0.102 mol), copper (II) acetate (46.0 g, 0.255 mol), and 3-thienylboronic acid (19.6 g, 0.153 mol) in CH$_2$Cl$_2$ (500 mL). The reaction mixture was stirred overnight, filtered through Celite®, rinsed with EtOAc/hexane (1:1, 300 mL), and concentrated in vacuo. The crude product was purified by column chromatography on silica using Hexane/EtOAc (1:1), giving the desired product (1.1 g, 50%).

Procedure B:

(3E)-3-[(4-METHYLPHENYL)IMINO]-1-(3-THIENYL)-1,3-DIHYDRO-2H-INDOL-2-ONE: A solution of 1-(3-thienyl)-1H-indole-2,3-dione (20 mg, 0.087 mmol) in 1% HOAc/MeOH (8 mL) was added to a solution of p-toluidine (19 mg, 0.18 mmol) in 1% HOAc/MeOH (8 mL). The reaction mixture was stirred for 12 h at room temperature, heated at 50° C. for 1 h, and concentrated in vacuo. The residue was purified by preparative TLC on silica using EtOAc/hexanes (3:7, 0.1% TEA) giving the desired product (14 mg, 50%).

Procedure C:

(3Z)-5-BROMO-3-{[3-(TRIFLUOROMETHYL)PHENYL]IMINO}-1,3-DIHYDRO-2H-INDOL-2-ONE: A mixture of 5-bromo-1H-indole-2,3-dione (1.0 g, 0.442 mmol) and 3-trifluoromethylaniline (0.993 g, 6.2 mmol) in a solution of 1% acetic acid in methanol was stirred at 50° C. for 12 h. The crude product was concentrated in vacuo, giving the desired crude product (640 mg, 40%).

Procedure D:

(3Z)-5-BROMO-1-PHENYL-3-{[3-TRIFLUOROMETHYL)PHENYL]IMINO}-1,3-DIHYDRO-2H-INDOL-2-ONE: A mixture of (3Z)-5-bromo-3-{[3-(trifluoromethyl)phenyl]imino}-1,3-dihydro-2H-indol-2-one (100 mg, 0.272 mmol), copper (II) acetate (54 mg, 0.33 mmol), triethylamine (82.8 mg, 0.817 mmol), and benzene boronic acid (40 mg, 0.325 mmol) in 5 mL of CH$_2$Cl$_2$ was stirred at room temperature for 12 h. The crude mixture was concentrated in vacuo and purified by preparative TLC using EtOAc:hexane (3:7, 1% triethylamine), giving the desired product (22 mg, 20%).

Procedure E:

(3Z)-1,5-DIPHENYL-3-{[3-(TRIFLUOROMETHYL) PHENYL]IMINO}-1,3-DIHYDRO-2H-INDOL-2-ONE: A mixture of (3Z)-5-bromo-1-phenyl-3-{[3-(trifluoromethyl) phenyl]imino}-1,3-dihydro-2H-indol-2-one (22 mg, 0.05 mmol), tetrakis(triphenylphosphine)palladium(0) (12.0 mg, 0.01 mmol), benzene boronic acid (10 mg, 0.08 mmol) in THF (5 mL), and aqueous $Na_2CO_3$ (2M, 100 μL) was heated at 67° C. for 24 h. The crude product was concentrated in vacuo and the residue was extracted with $CH_2Cl_2$ (3×1 ml), concentrated, and purified by preparative TLC using 10% methanol in $CHCl_3$, giving the desired product (4 mg, 18%).

Procedure F:

1-[(5-CHLORO-1-BENZOTHIEN-3-YL)METHYL]-2H-INDOLE-2,3-DIONE: A solution of isatin (125 mg, 0.85 mmol) in anhydrous dioxane (10 mL) was added dropwise to a solution of sodium hydride (60% dispersion in mineral oil, 25 mg, 0.62 mmol) in anhydrous dioxane (10 mL) at 0° C. under argon. The mixture was allowed to stir for 5 minutes and then a solution of 3-(bromomethyl)-5-chlorobenzo[b] thiophene (267 mg, 1.02 mmol) in dioxane (10 mL) was added dropwise to the reaction mixture. The reaction mixture was heated at reflux under argon for 16 h and concentrated in vacuo. The crude material was purified by preparative TLC using 1:24 methanol in chloroform as the eluent, giving the desired product as a yellow solid (125 mg, 0.38 mmol, 45%).

Procedure G:

1-[(5-CHLORO-1-BENZOTHIEN-3-YL)METHYL]-3-{[3-(TRIFLUOROMETHYL)PHENYL]IMINO}-1,3-DIHYDRO-2H-INDOL-2-ONE: A mixture of 1-[(5-chloro-1-benzothien-3-yl)methyl]-2H-indole-2,3-dione (50 mg, 0.15 mmol) and 3-trifluoromethylaniline (0.020 mL, 0.15 mmol) was heated neat at 140° C. for 2 h. The crude material was purified by preparative TLC using a mixture of 1:3 ethyl acetate and hexane as the eluent giving the desired product as a yellow solid (13 mg, 0.030 mmol, 18%).

Procedure H:

6-METHOXY-1-PHENYL-1H-INDOLE-2,3-DIONE: A solution of N-(3-methoxyphenyl)-N-phenylamine (1.14 g, 5.72 in ether (3 mL) was added to a solution of oxalyl chloride (728 g, 5.75 mmol) and heated at reflux for 1 h. The resulting mixture was cooled to room temperature, concentrated to dryness, and redissolved in nitrobenzene (35 mL). The solution was added to a solution of $AlCl_3$ in nitrobenzene (0.762 g, 5.72 mmol), and the resulting mixture was heated at 70° C. for 16 h. The crude product was concentrated in vacuo and purified by column chromatography using EtOAc/hexane (1:1), giving the desired product 60, mg, 50%).

Compounds 2-17, inclusive, were purchased from Bionet Research Ltd., 3 Highfield Industrial Estate, Camelford, Cornwall PL32 9QZ, UK. These compounds can also be synthesized using the General Procedure described above.

Compound 1: 3-[(2-METHOXYPHENYL)IMINO]-1-PHENYL-1,3-DIHYDRO-2H-INDOL-2-ONE

Compound 2: 1-PHENYL-3-[[3-(TRIFLUOROMETHYL)PHENYL]IMINO]-1,3-DIHYDRO-2H-INDOL-2-ONE Compound 3: 3-[(3-METHYLPHENYL)IMINO]-1-PHENYL-1,3-DIHYDRO-2H-INDOL-2-ONE Compound 4: 3-[(3-CHLOROPHENYL)IMINO]-1-PHENYL-1,3-DIHYDRO-2H-INDOL-2-ONE Compound 5: 1-PHENYL-3-[[4-(TRIFLUOROMETHYL)PHENYL]IMINO]-1,3-DIHYDRO-2H-INDOL-2-ONE Compound 6: 3-[(4-METHYLPHENYL)IMINO]-1-PHENYL-1,3-DIHYDRO-2H-INDOL-2-ONE Compound 7: 3-[(4-CHLOROPHENYL)IMINO]-1-PHENYL-1,3-DIHYDRO-2H-INDOL-2-ONE Compound 8: 3-[(4-BROMOPHENYL)IMINO]-1-PHENYL-1,3-DIHYDRO-2H-INDOL-2-ONE Compound 9: 3-[(4-FLUOROPHENYL)IMINO]-1-PHENYL-1,3-DIHYDRO-2H-INDOL-2-ONE Compound 10: 3-[(4-PHENOXYPHENYL)IMINO]-1-PHENYL-1,3-DIHYDRO-2H-INDOL-2-ONE Compound 11: 3-[(4-ETHOXYPHENYL)IMINO]-1-PHENYL-1,3-DIHYDRO-2H-INDOL-2-ONE Compound 12: 3-[(4-METHOXYPHENYL)IMINO]-1-PHENYL-1,3-DIHYDRO-2H-INDOL-2-ONE Compound 13: 3-[(3,5-DICHLOROPHENYL)IMINO]-1-PHENYL-1,3-DIHYDRO-2H-INDOL-2-ONE Compound 14: 3-[(3,5-DIMETHYLPHENYL)IMINO]-1-PHENYL-1,3-DIHYDRO-2H-INDOL-2-ONE Compound 15: 1-ALLYL-3-[(3,4-DICHLOROPHENYL)IMINO]-1,3-DIHYDRO-2H-INDOL-2-ONE Compound 16: 1-ALLYL-3-[(3,5-DICHLOROPHENYL)IMINO]-1,3-DIHYDRO-2H-INDOL-2-ONE Compound 17: 3-[(4-BROMOPHENYL)IMINO]-1-ISOPROPYL-1,3-DIHYDRO-2H-INDOL-2-ONE Compound 18: 1-[(5-CHLORO-2-THIENYL)METHYL]-3-{[3-(TRIFLUOROMETHYL)PHENYL] IMINO}-1,3-DIHYDRO-2H-INDOL-2-ONE: A mixture of 1-[(5-chloro-2-thienyl)methyl]-2H-indole-2,3-dione (25 mg, 0.09 mmol) (prepared as described below) and 3-trifluoromethylaniline (11.3 μL, 0.09 mmol) was heated neat at 140° C. for 2 h. The crude material was purified by preparative TLC using a mixture of 3:7 ethyl acetate in hexane as the eluent, giving the desired product (23 mg, 0.05 mmol, 61%). $^1$H NMR (400 MHz): δ (major isomer) 7.57 (t, J=7.7, 1H), 7.53 (t, J=7.8, 1H), 7.33 (t, J=7.8, 1H), 7.28 (s, 1H), 7.19 (d, J=7.6, 2H), 6.94-6.72 (m, 4H), 6.56 (d, J=7.7, 1H), 5.02 (s, 2H); ESI-MS m/z found 421 (MH$^+$).

1-[(5-CHLORO-2-THIENYL)METHYL]-2H-INDOLE-2,3-DIONE: A solution of isatin (125 mg, 0.85 mmol) in anhydrous dioxane (10 mL) was added dropwise to a solution of sodium hydride (60% dispersion in mineral oil, 24 mg, 0.62 mmol) in anhydrous dioxane (10 mL) at 0° C. under argon. The mixture was allowed to stir for 5 minutes and then 2-chloro-5-(chloromethyl)thiophene (0.12 mL, 1.02 mmol) in dioxane (10 mL) was added dropwise to the resulting mixture. The reaction mixture was heated at reflux under argon for 16 h and concentrated in vacuo. The crude material was purified by preparative TLC using 1:24 methanol in chloroform as the eluent, giving the desired product as a yellow solid (53 mg, 0.19 mmol, 22%). $^1$H NMR (400 MHz): δ 7.62 (d, J=7.4, 1H), 7.56 (t, J=7.8, 1H), 7.14 (t, J=7.7, 1H), 6.94 (d, J=8.0, 1H), 6.90 (d, J=3.2, 1H), 6.78 (d, J=3.7, 1H), 4.90 (s, 2H).

Compound 19: 1-(3-THIENYL)-3-{[3-(TRIFLUOROMETHYL)PHENYL]IMINO}-1,3-DIHYDRO-2H-INDOL-2-ONE: A mixture of 1-(3-thienyl)-2H-indole-2,3-dione (25 mg, 0.11 mmol) (prepared as described below) and 3-trifluoromethylaniline (14 uL, 0.11 mmol) was heated neat at 140° C. for 2 h. The crude material was purified by preparative TLC using a mixture of 3:7 ethyl acetate and hexane as the eluent, giving the desired product as a yellow solid (7.3 mg, 0.02 mmol, 22%). $^1$H NMR (400 MHz) δ 7.62-7.19 (m, 9H), 6.94 (d, J=8.0, 1H), 6.76 (t, J=7.6, 1H); ESI-MS m/z found 373 (MH$^+$).

1-(3-THIENYL)-2H-INDOLE-2,3-DIONE: Copper(II) acetate monohydrate (4.25 g, 23.4 mmol) was heated at reflux in acetic anhydride (30 mL) for 2 h. The mixture was filtered and washed with anhydrous ether (500 mL). The solid was dried in vacuo at 55° C. for 16 h. Dichloromethane (1 mL) was added to a mixture of copper(II) acetate (62 mg, 0.34 mmol), isatin (50 mg, 0.34 mmol), and thiophene-3-boronic acid (87 mg, 0.68 mmol), followed by triethylamine (0.10 mL, 0.68 mmol) under argon. The resulting solution was stirred for 16 h at room temperature. The reaction mixture was then recharged with 0.10 mmol copper(II) acetate, 0.10 mmol of 3-thiophene boronic acid, and 1 drop of triethylamine, and the mixture was heated at 50° C. for 6 h. The crude material was purified by preparative TLC using 3:97 methanol in chloroform as the eluent, giving the desired product as a yellow solid (25 mg, 0.11 mmol, 33%). $^1$H NMR (400 MHz): δ 7.70 (d, J=7.5, 1H), 7.58 (t, J=7.8, 1H), 7.50 (d, J=5.1, 1H), 7.48 (s, 1H), 7.24 (d, J=5.1, 1H), 7.18 (t, J=7.51, 1H), 7.05 (d, J=8.0, 1H).

Compound 20: 2-METHYL-5-[(2-OXO-1-PHENYL-1,2-DIHYDRO-3H-INDOL-3-YLIDENE)AMINO]-2H-ISOINDOLE-1,3(2H)-DIONE: A mixture of 1-phenylisatin (50 mg, 0.22 mmol) and 4-amino-N-methylpthalimide (40 mg, 0.22 mmol) was heated neat at 215° C. for 2 h. The crude material was purified by preparative TLC using a mixture of 3:7 ethyl acetate and hexane as the eluent, giving the desired product as a yellow solid (8 mg, 0.02 mmol, 10%). $^1$H NMR (400 MHz): δ 7.88 (d, J=7.8, 1H), 7.83-7.80 (m, 1H), 7.51 (t, J=7.5, 1H), 7.47-7.18 (m, 6H), 7.02 (t, J=8.0, 1H), 6.91-6.79 (m, 2H), 6.58 (d, J=7.5, 1H), 3.22 (s, 3H); ESI-MS m/z found 382 (MH$^+$).

Compound 21: 1-[(5-CHLORO-1-BENZOTHIEN-3-YL)METHYL]-3-{[3-(TRIFLUOROMETHYL)PHENYL]IMINO}-1,3-DIHYDRO-2H-INDOL-2-ONE: 1-[(5-CHLORO-1-BENZOTHIEN-3-YL)METHYL]-2H-INDOLE-2,3-DIONE was prepared by Procedure F. $^1$H NMR (400 MHz): δ 7.89 (s, 1H), 7.79 (d, J=8.5, 1H), 7.65 (d, J=7.5, 1H), 7.54 (t, J=8.0, 1H), 7.42 (s, 1H), 7.38 (d, J=8.5, 1H), 7.14 (t, J=7.5, 1H), 6.88 (d, J=7.8, 1H), 5.13 (s, 2H). From this intermediate, 1-[(5-CHLORO-1-BENZOTHIEN-3-YL)METHYL]-3-{[3-(TRIFLUOROMETHYL)PHENYL]-IMINO}-1,3-DIHYDRO-2H-INDOL-2-ONE was prepared by Procedure G. $^1$H NMR (400 MHz): δ 7.98 (d, J=2.0, 1H), 7.80 (d, J=8.6, 1H), 7.58 (t, J=7.7, 1H), 7.52 (d, J=8.1, 1H), 7.43 (s, 1H), 7.38 (dd, J=8.6, 1.9, 1H), 7.31 (overlapping singlet and dt, J=1.2, 7.8, 2H), 7.24 (d, J=7.8, 1H), 6.87 (d, J=7.9, 1H), 6.77 (t, J=7.7, 1H), 6.59 (d, J=7.7, 1H), 5.20 (s, 2H). ESI-MS m/z found 471 (MH$^+$ with $^{35}$Cl), 473 (MH$^+$ with $^{37}$Cl).

Compound 22: 3-(1H-INDOL-5-YLIMINO)-1-PHENYL-1,3-DIHYDRO-2H-INDOL-2-ONE: 1-Phenylisatin (51.8 mg, 0.23 mmol) and 5-aminoindole (31 mg, 0.23 mmol) were mixed and heated at 140° C. for 2 h. The resulting crude product was purified by preparative TLC using ethyl acetate/hexane (6:4) as the eluent, giving the desired product as a yellow solid (10.8 mg, 14%). $^1$H NMR (400 MHz): δ 8.28 (s, 1H), 7.57 (t, J=7.7, 2H), 7.49-7.40 (m, 6H), 7.29-7.23 (m, 1H), 7.03 (dd, J=8.5, 1.7, 1H), 6.98 (d, J=7.6, 1H), 6.83 (d, J=8.0, 1H), 6.74, J=7.6, 1H), 6.59 (s, 1H); ESI-MS m/z found 338 (MH$^+$).

Compound 23: 3-[(6-CHLORO-3-PYRIDINYL)IMINO]-1-PHENYL-1,3-DIHYDRO-2H-INDOL-2-ONE: 1-Phenylisatin (23.0 mg, 0.10 mmol) and 5-amino-2-chloropyridine (12.8 mg, 0.10 mmol) were mixed and heated at 140° C. for 7 h. The resulting crude product was purified by preparative TLC using hexane/ethyl acetate (8:2) as the eluent, giving the desired product as a yellow solid (19.7 mg, 59%). $^1$H NMR (400 MHz) δ 8.15 (d, J=8, 1H), 7.6-7.2 (m, 9H), 6.85-6.75 (m, 2H); ESI-MS m/z found 334 (MH$^+$).

Compound 24: 3-[(2-METHYL-1,3-BENZOTHIAZOL-5-YL)IMINO]-1-PHENYL-1,3-DIHYDRO-2H-INDOL-2-ONE: 5-Amino-2-methylbenzothiazole (52.2 mg, 0.31 mmol) was mixed with 1-phenylisatin (69.7 mg, 0.31 mmol) and heated at 140° C. for 3 h. The resulting crude product was purified by preparative TLC using ethyl acetate/hexane (6:4) as the eluent to give the desired product as a yellow solid (36.9 mg, 32.3%). $^1$H NMR: δ 7.9-6.7 (m, 12H), 2.9 (s, 3H). ESI-MS m/z found 370 (MH$^+$).

Compound 25: (3Z)-3-[(3,4-DICHLOROPHENYL)IMINO]-1-(2-PYRIDINYLMETHYL)-1,3-DIHYDRO-2H-INDOL-2-ONE: Prepared by Procedures F (for substitution of 2-picolyl chloride) and G. $^1$H NMR (400 MHz, CDCl$_3$) δ 8.51-8.46 (m, 1H), 7.87-7.78 (m, 1H), 7.64 (d, 1H, J=7.1), 7.53-7.31 (m, 5H), 7.28 (d, 1H, J=4.1), 7.12 (d, 1H, J=8.1), 6.58-6.53 (m, 1H), 5.51 (s, 2H); ESI-MS m/z 381 (MH$^+$).

Compound 26: (3Z)-3-[(3,4-DICHLOROPHENYL)IMINO]-1-[(3,5-DIMETHYL-4-ISOXAZOLYL)METHYL]-1,3-DIHYDRO-2H-INDOL-2-ONE: Prepared by Procedures F (for substitution of 4-chloromethyl-3,5-dimethylisoxazole) and B (microwave heating). $^1$H NMR (400 MHz, CDCl$_3$) δ 7.63 (d, 1H, J=9.1), 7.46 (dt, 1H, J=8.1, 2.0), 7.28 (d, 1H, J=2.1), 7.02 (d, 1H, J=2.0), 6.88 (dt, 1H, J 8.0, 2.1), 6.74-6.72 (m, 1H), 6.72-6.70 (m, 1H), 5.53 (s, 2H), 2.50 (s, 3H), 2.24 (s, 3H); ESI-MS m/z 399 (MH$^+$).

Compound 27: (3Z)-3-[(3,4-DICHLOROPHENYL)IMINO]-1-[3-(TRIFLUOROMETHYL)PHENYL]-1,3-DIHYDRO-2H-INDOL-2-ONE: Prepared by Procedures A and B. $^1$H NMR (400 MHz, CDCl$_3$) δ 7.90-7.87 (m, 1H), 7.83-7.79 (m, 1H), 7.67 (d, 1H, J=8), 7.46-7.40 (m, 1H), 7.33 (d, 1H, J=2), 7.08-7.05 (m, 1H), 6.96-6.80 (m, 5H); ESI-MS m/z 435 (MH$^+$).

Compound 28: (3Z)-1-(3,5-DICHLOROPHENYL)-3-[(3,4-DICHLOROPHENYL)IMINO]-1,3-DIHYDRO-2H-INDOL-2-ONE: Prepared by Procedures A and B. $^1$H NMR (400 MHz, CDCl$_3$) δ 7.93 (d, 1H, J=8.1), 7.79 (d, 1H, J=6.0), 7.72-7.68 (m, 1H), 7.59-7.45 (m, 1H), 7.46 (d, 1H, J=8.1), 7.32 (dt, 1H, J=8.0, 2.1), 7.23 (d, 1H, J=2.5), 6.97 (dd, 1H, J=8.0, 2.1), 6.92-6.87 (m, 1H), 6.85-6.81 (m, 1H); ESI-MS m/z 435 (MH$^+$).

Compound 29: (3Z)-3-[(3,4-DICHLOROPHENYL)IMINO]-6-METHOXY-1-PHENYL-1,3-DIHYDRO-2H-INDOL-2-ONE: Prepared by Procedures H and B. $^1$H NMR (400 MHz, CDCl$_3$) δ 7.69-7.54 (m, 1H), 7.53-7.38 (m, 3H), 7.29 (d, 1H, J=2.0), 7.17 (d, 1H, J=8.1), 7.12 (d, 1H, J=8.0), 6.84 (d, 1H, J=2.5), 6.78 (d, 1H, J=8), 6.6 (dd, 2H, J=8.0, 2.0), 6.55 (dd, 2H, J=8.1, 2.5); ESI-MS m/z (398 MH$^+$).

Compound 30: (3Z)-3-[(4-CHLORO-3-METHYLPHENYL)IMINO]-1-(3-THIENYL)-1,3-DIHYDRO-2H-INDOL-2-ONE: Prepared by Procedures A and B (80° C.). $^1$H NMR (400 MHz, CDCl$_3$) δ 7.69-7.62 (m, 2H), 7.49 (s, 1H), 7.47 (s, 1H), 7.41 (dt, 1H, J=7.1, 1.6), 7.3 (dd, 1H, J=5.0, 1.6), 7.05-6.97 (m, 1H, 6.93-6.86 (m, 1H), 6.77 (m, 1H), 6.56 (m, 1H), 2.53 (s, 3H); ESI-MS m/z 353 (MH$^+$).

Compound 31: (3Z)-3-(2-NAPHTHYLIMINO)-1-(3-THIENYL)-1,3-DIHYDRO-2H-INDOL-2-ONE: Prepared by Procedures A and B (80° C.). $^1$H NMR (400 MHz, CDCl$_3$) δ 8.15 (d, 1H, J=9.1), 8.06-7.99 (m, 1H), 7.89-7.80 (m, 1H), 7.78-7.71 (m, 1H), 7.71-7.47 (m, 4H), 7.41-7.35 (m, 1H), 7.33 (d, 1H, J=5.2), 7.28 (d, 1H, J=6.8.1), 7.00 (d, 1H, J=8.0), 6.76 (t, 1H, J=7.8), 6.67 (d, 1H, J=7.9); ESI-MS m/z 355 (MH$^+$).

Compound 32: (3Z)-3-[(4-CHLOROPHENYL)IMINO]-1-(3-THIENYL)-1,3-DIHYDRO-2H-INDOL-2-ONE: Prepared by Procedures A and B (80° C.). $^1$H NMR (400 MHz, CDCl₃) δ 7.69-7.56 (m, 2H), 7.54-7.48 (m, 1H), 7.41 (dt, 1H, J=8, 2), 7.32-7.28 (m, 1H), 7.11-6.99 (m, 3H), 6.89 (dt, 1H, J=8), 6.77-6.73 (m, 1H), 6.66-6.33 (m, 1H); ESI-MS m/z 339 (MH⁺).

Compound 33: (3Z)-3-[(4-IODOPHENYL)IMINO]-1-(3-THIENYL)-1,3-DIHYDRO-2H-INDOL-2-ONE: Prepared by Procedures A and B (1% HOAc in MeOH). ¹H NMR (400 MHz, CDCl₃) δ 7.79-7.74 (m, 2H), 7.53-7.48 (m, 2H), 7.35 (dt, 1H, J=8.0, 1.2), 7.29-7.24 (m, 1H), 6.98 (d, 1H, J=8.0), 6.89-6.75 (m, 4H); ESI-MS m/z 431 (MH⁺).

Compound 34: (3Z)-3-[(4-METHYLPHENYL)IMINO]-1-(3-THIENYL)-1,3-DIHYDRO-2H-INDOL-2-ONE: Prepared by Procedures A and B (1% HOAc in MeOH). ¹H NMR (400 MHz, CDCl₃) δ 7.52-7.44 (m, 2H), 7.35-7.22 (m, 4H), 6.99-6.93 (m, 3H), 6.87-6.78 (m, 2H), 2.42 (s, 3H); ESI-MS m/z 319 (MH⁺).

Compound 35: (3Z)-3-[(3,5-DIFLUOROPHENYL)IMINO]-1-(3-THIENYL)-1,3-DIHYDRO-2H-INDOL-2-ONE: Prepared by Procedures A and B (1% HOAc in MeOH). ¹H NMR (400 MHz, CDCl₃) δ 7.54-7.16 (m, 4H), 6.99 (dt, 1H, J=8.2, 0.8), 6.89 (dt, 1H, J=7.7, 1.1), 6.76 (d, 1H, J=7.5), 6.71 (tt, 1H, J=9.3, 2.3), 6.64-6.57 (m, 2H); ESI-MS m/z 341 (MH⁺).

Compound 36: ETHYL 3-{[(3Z)-2-OXO-1-(3-THIENYL)-1,2-DIHYDRO-3H-INDOL-3-YLIDENE]AMINO}BENZOATE: Prepared by Procedures A and B (1% HOAc in MeOH). ¹H NMR (400 MHz, CDCl₃) δ 7.96 (d, 1H, J=7.4), 7.75-7.17 (m, 6H), 6.98 (d, 1H, J=8.0), 6.87-6.78 (m, 2H), 6.63 (d, 1H, J=7.8), 4.45-4.32 (m, 2H), 1.43-1.33 (m, 3H); ESI-MS m/z 377 (MH⁺).

Compound 37: (3Z)-3-[(6-CHLORO-3-PYRIDINYL)IMINO]-1-(3-THIENYL)-1,3-DIHYDRO-2H-INDOL-2-ONE: Prepared by Procedures A and B (1% HOAc in MeOH). ¹H NMR (400 MHz, CDCl₃) δ 8.21-6.81 (m, 10H); ESI-MS m/z 340 (MH⁺).

Compound 38: 3Z)-3-[(4-PHENOXYPHENYL)IMINO]-1-(3-THIENYL)-1,3-DIHYDRO-2H-INDOL-2-ONE: Prepared by Procedures A and B (1% HOAc in MeOH). ¹H NMR (400 MHz, CDCl₃) δ 7.85-6.70 (m, 16H); ESI-MS m/z 397 (MH⁺).

Compound 39: (3Z)-3-[(4-BROMOPHENYL)IMINO]-1-(3-THIENYL)-1,3-DIHYDRO-2H-INDOL-2-ONE: Prepared by Procedures A and G. ¹H NMR (400 MHz, CDCl₃) δ 7.82-6.55 (m, 11H); ESI-MS m/z 383 (MH⁺).

Compound 40: (3Z)-3-[(3-CHLOROPHENYL)IMINO]-1-(3-THIENYL)-1,3-DIHYDRO-2H-INDOL-2-ONE: Prepared by Procedures A and G. ¹H NMR (400 MHz, CDCl₃) δ 7.55-6.50 (m, 11H); ESI-MS m/z 339 (MH⁺).

Compound 41: (3Z)-3-[(3-METHYLPHENYL)IMINO]-1-(3-THIENYL)-1,3-DIHYDRO-2H-INDOL-2-ONE: Prepared by Procedures A and B (1% HOAc in MeOH). ¹H NMR (400 MHz, CDCl₃) δ 7.67-6.78 (m, 11H), 2.39 (s, 3H); ESI-MS m/z 319 (MH⁺).

Compound 42: (3Z)-3-[(3,4-DICHLOROPHENYL)IMINO]-1-(3-THIENYL)-1,3-DIHYDRO-2H-INDOL-2-ONE: Prepared by Procedures A and B (1% HOAc in MeOH). ¹H NMR (400 MHz, CDCl₃) δ 7.82-6.80 (m, 10H); ESI-MS m/z 373 (MH⁺).

Compound 43: (3Z)-1-(2-PYRIDINYLMETHYL)-3-{[3-(TRIFLUOROMETHYL)PHENYL]IMINO}-1,3-DIHYDRO-2H-INDOL-2-ONE: Prepared by Procedure B. ESI-MS m/z 382 (MH⁺).

Compound 44: (3Z)-3-[(3,5-DICHLOROPHENYL)IMINO]-1-(2-PYRIDINYLMETHYL)-1,3-DIHYDRO-2H-INDOL-2-ONE: Prepared by Procedure B. ESI-MS m/z 382 (MH⁺).

Compound 45: (3Z)-1-[(3,5-DIMETHYL-4-ISOXAZOLYL)METHYL]-3-{[3-(TRIFLUOROMETHYL)PHENYL]IMINO}-1,3-DIHYDRO-2H-INDOL-2-ONE: Prepared by Procedure B. ESI-MS m/z 400 (MH⁺).

Compound 46: (3Z)-3-[(3,4-DIFLUOROPHENYL)IMINO]-1-(3-PYRIDINYLMETHYL)-1,3-DIHYDRO-2H-INDOL-2-ONE: Prepared by Procedures F (for substitution of 3-picolylchloride) and B. ESI-MS m/z 350 (MH⁺).

Compound 47: (3Z)-1-(3-PYRIDINYLMETHYL)-3-{[3-(TRIFLUOROMETHYL)PHENYL]IMINO}-1,3-DIHYDRO-2H-INDOL-2-ONE: Prepared by Procedure B. ESI-MS m/z 382 ((MH⁺).

Compound 48: (3Z)-3-[(3,4-DIFLUOROPHENYL)IMINO]-1-(2-PYRIDINYLMETHYL)-1,3-DIHYDRO-2H-INDOL-2-ONE: Prepared by Procedure B. ESI-MS m/z 350 (MH⁺).

Compound 49: (3Z)-3-[(3,5-DICHLOROPHENYL)IMINO]-1-(3-PYRIDINYLMETHYL)-1,3-DIHYDRO-2H-INDOL-2-ONE: Prepared by Procedure B. ESI-MS m/z 384 (MH⁺).

Compound 50: (3Z)-3-[(3,5-DICHLOROPHENYL)IMINO]-1-[(3,5-DIMETHYL-4-ISOXAZOLYL)METHYL]-1,3-DIHYDRO-2H-INDOL-2-ONE: Prepared by Procedure B. ESI-MS m/z 402 (MH⁺).

Compound 51: (3Z)-1-PHENYL-3-(5-QUINOLINYLIMINO)-1,3-DIHYDRO-2H-INDOL-2-ONE: Prepared by Procedure G. ¹H NMR (400 MHz, CDCl₃) δ 9.38-9.32 (m, 1H), 8.55-8.50 (m, 1H), 8.01-6.62 (m, 12H), 6.43-6.35 (m, 1H); ESI-MS m/z 350 (MH⁺).

Compound 52: (3Z)-3-[(4-IODOPHENYL)IMINO]-1-PHENYL-1,3-DIHYDRO-2H-INDOL-2-ONE: Prepared by Procedure B (0.1% HOAc, 80° C., 92 h, 4 eq RNH₂, 3 Å molecular sieves). ESI-MS m/z 425 (MH⁺).

Compound 53: (3Z)-3-[(3,4-DIFLUOROPHENYL)IMINO]-1-PHENYL-1,3-DIHYDRO-2H-INDOL-2-ONE: Prepared by Procedure B (0.1% HOAc, 80° C., 92 h, 4 eq RNH₂, 3 Å molecular sieves). ESI-MS m/z 335 (MH⁺).

Compound 54: (3Z)-3-[(2-CHLORO-4-METHYLPHENYL)IMINO]-1-PHENYL-1,3-DIHYDRO-2H-INDOL-2-ONE: Prepared by Procedure B (0.1% HOAc, 80° C., 92 h, 4 eq RNH₂, 3 Å molecular sieves). ESI-MS m/z 347 (MH⁺ with ³⁵Cl), 349 (MH⁺ with ³⁷Cl).

Compound 55: (3Z)-3-[(2,4-DIMETHOXYPHENYL)IMINO]-1-PHENYL-1,3-DIHYDRO-2H-INDOL-2-ONE: Prepared by Procedure B (0.1% HOAc, 80° C., 92 h, 4 eq RNH₂, 3 Å molecular sieves). ESI-MS m/z 359 (MH⁺).

Compound 56: 3-{[(3Z)-2-OXO-1-PHENYL-1,2-DIHYDRO-3H-INDOL-3-YLIDENE]AMINO}BENZONITRILE: Prepared by Procedure B (0.1% HOAc, 80° C., 92 h, 4 eq RNH₂, 3 Å molecular sieves). ESI-MS m/z 324 (MH⁺).

Compound 57: (3Z)-3-{[2-METHYL-5-(TRIFLUOROMETHYL)PHENYL]IMINO}-1-PHENYL-1,3-DIHYDRO-2H-INDOL-2-ONE: Prepared by Procedure B (0.1% HOAc, 80° C., 92 h, 4 eq RNH₂, 3 Å molecular sieves). ESI-MS m/z 381 (MH⁺).

Compound 58: (3Z)-3-[(4-CHLORO-3-METHYLPHENYL)IMINO]-1-(3-THIENYL)-1,3-DIHYDRO-2H-INDOL-2-ONE: Prepared by Procedures A and B (80° C.). ESI-MS m/z 353 (MH⁺).

Compound 59: (3Z)-3-(6-QUINOLINYLIMINO)-1-(3-THIENYL)-1,3-DIHYDRO-2H-INDOL-2-ONE: Prepared by Procedures A and B (80° C.). ESI-MS m/z 356 (MH+).

Compound 60: (3Z)-3-[(4-CHLOROPHENYL)IMINO]-1-(3-THIENYL)-1,3-DIHYDRO-2H-INDOL-2-ONE: Prepared by Procedures A and B (80° C.). ESI-MS m/z 339 (MH+).

Compound 61: (3Z)-3-[(3-ISOPROPYLPHENYL)IMINO]-1-(3-THIENYL)-1,3-DIHYDRO-2H-INDOL-2-ONE: Prepared by Procedures A and B (80° C.). ESI-MS m/z 347 (MH+).

Compound 62: (3Z)-3-[(4-CYCLOHEXYLPHENYL)IMINO]-1-(3-THIENYL)-1,3-DIHYDRO-2H-INDOL-2-ONE: Prepared by Procedures A and B (80° C.). ESI-MS m/z 387 (MH+).

Compound 63: (3Z)-3-(1,3-BENZOTHIAZOL-6-YLIMINO)-1-PHENYL-1,3-DIHYDRO-2H-INDOL-2-ONE: Prepared by Procedure G. ESI-MS m/z 356 (MH+).

Compound 64: (3Z)-3-(1H-INDAZOL-6-YLIMINO)-1-PHENYL-1,3-DIHYDRO-2H-INDOL-2-ONE: Prepared by Procedure G. ESI-MS m/z 339 (MH+).

Compound 65: (3Z)-3-[(3-CHLOROPHENYL)IMINO]-6-METHOXY-1-PHENYL-1,3-DIHYDRO-2H-INDOL-2-ONE: Prepared by Procedures H and G. ESI-MS m/z 363 (MH+).

Compound 66: (3Z)-6-METHOXY-1-PHENYL-3-{[3-(TRIFLUOROMETHYL)PHENYL]IMINO}-1,3-DIHYDRO-2H-INDOL-2-ONE: Prepared by Procedures H and G. ESI-MS m/z 397 (MH+).

Compound 67: (3Z)-3-[(3-BROMOPHENYL)IMINO]-1-PHENYL-1,3-DIHYDRO-2H-INDOL-2-ONE: Prepared by Procedure B. ESI-MS m/z 378 (MH+).

Compound 68: (3Z)-1,5-DIPHENYL-3-{[3-(TRIFLUOROMETHYL)PHENYL]IMINO}-1,3-DIHYDRO-2H-INDOL-2-ONE: Prepared by Procedures C, D, and E. ESI-MS m/z 443 (MH+).

Compound 69: (3Z)-1-(4-HYDROXYPHENYL)-3-{[3-(TRIFLUOROMETHYL)PHENYL]IMINO}-1,3-DIHYDRO-2H-INDOL-2-ONE: Prepared by Procedures G (6 eq of aniline) and D. ESI-MS m/z 383 (MH+).

Compound 70: (3Z)-3-[(3,4-DICHLOROPHENYL)IMINO]-1-(3-PYRIDINYLMETHYL)-1,3-DIHYDRO-2H-INDOL-2-ONE: Prepared by Procedure G (75° C., 2 h). ESI-MS m/z 383 (MH+).

Compounds 1-70 as described above are merely illustrative of indolone compounds which may be utilized in the methods of the present invention. Further indolone compounds may be obtained utilizing the methods shown in Schemes 1-5 and procedures generally known in the art.

It may be necessary to incorporate protection and deprotection strategies for substituents such as amino, amido, carboxylic acid, and hydroxyl groups in the synthetic methods described above to form indolone derivatives. Methods for protection and deprotection of such groups are well-known in the art, and may be found, for example in Green, T. W. and Wuts, P. G. M. (1991) Protection Groups in Organic Synthesis, 2nd Edition John Wiley & Sons, New York.

The structures of Compounds 1-70 are illustrated in Tables 1 and 1a.

TABLE 1

Chemical Structures of Compounds

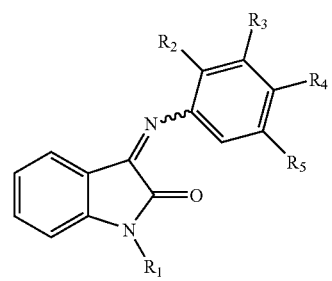

| Compound | R1 | R2 | R3 | R4 | R5 |
|---|---|---|---|---|---|
| 1 | Ph | OMe | H | H | H |
| 2 | Ph | H | CF$_3$ | H | H |
| 3 | Ph | H | Me | H | H |
| 4 | Ph | H | Cl | H | H |
| 5 | Ph | H | H | CF$_3$ | H |
| 6 | Ph | H | H | Me | H |
| 7 | Ph | H | H | Cl | H |
| 8 | Ph | H | H | Br | H |
| 9 | Ph | H | H | F | H |
| 10 | Ph | H | H | OPh | H |
| 11 | Ph | H | H | OEt | H |
| 12 | Ph | H | H | OMe | H |
| 13 | Ph | H | Cl | H | Cl |
| 14 | Ph | H | Me | H | Me |
| 15 | Allyl | H | Cl | Cl | H |
| 16 | Allyl | H | Cl | H | Cl |
| 17 | Isopropyl | H | H | Br | H |

| Compound | Structure |
|---|---|
| 18 | 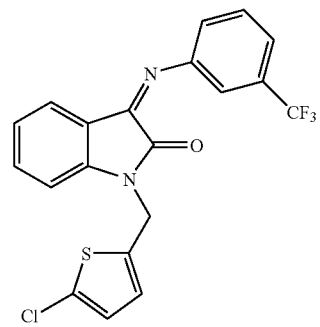 |
| 19 | 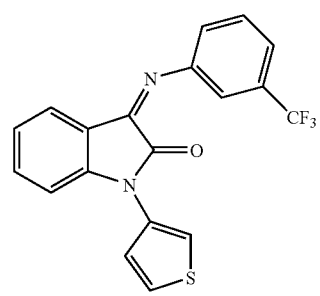 |

TABLE 1-continued

Chemical Structures of Compounds

| # | Structure description |
|---|---|
| 20 | 1-phenyl-3-[(2-methyl-1,3-dioxoisoindolin-5-yl)imino]indolin-2-one |
| 21 | 1-[(6-chlorobenzo[b]thiophen-2-yl)methyl]-3-[(3-trifluoromethylphenyl)imino]indolin-2-one |
| 22 | 1-phenyl-3-[(1H-indol-5-yl)imino]indolin-2-one |
| 23 | 1-phenyl-3-[(6-chloropyridin-3-yl)imino]indolin-2-one |
| 24 | 1-phenyl-3-[(2-methylbenzo[d]thiazol-5-yl)imino]indolin-2-one |
| 25 | 1-(pyridin-2-ylmethyl)-3-[(3,4-dichlorophenyl)imino]indolin-2-one |
| 26 | 1-[(3-methylisoxazol-4-yl)methyl]-3-[(3,4-dichlorophenyl)imino]indolin-2-one |

TABLE 1-continued
Chemical Structures of Compounds
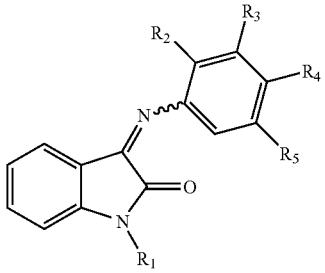
| 27 | 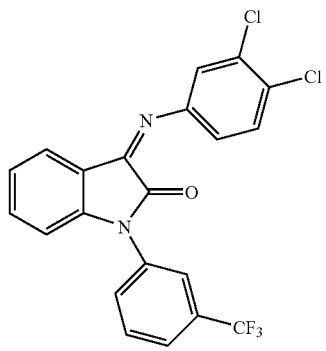 |
|---|---|
| 28 | 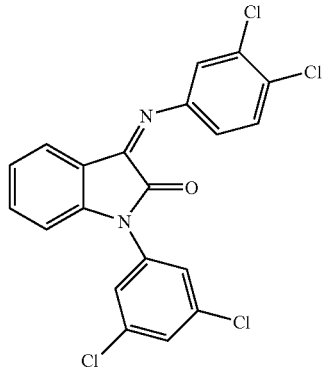 |
| 29 | 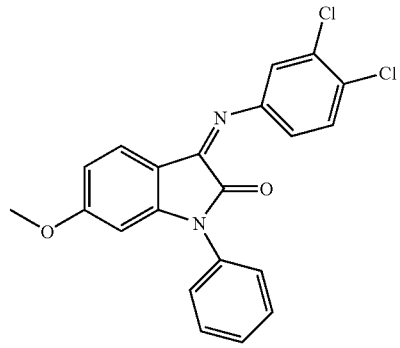 |
TABLE 1-continued
Chemical Structures of Compounds
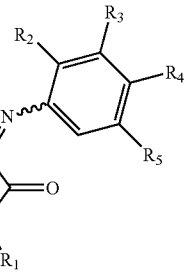
| 30 | 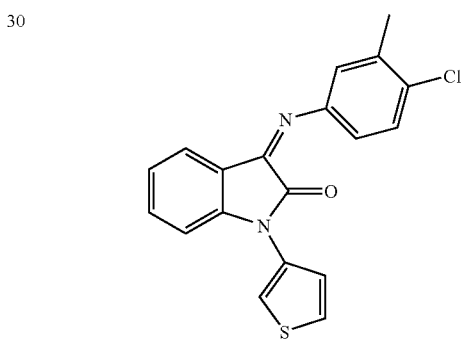 |
|---|---|
| 31 | 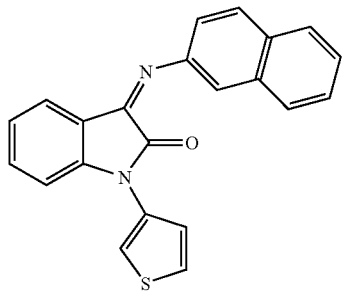 |
| 32 | 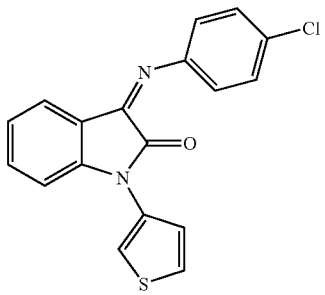 |
| 33 | 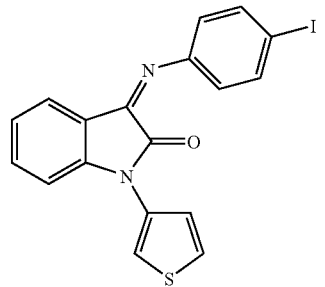 |

TABLE 1-continued
Chemical Structures of Compounds
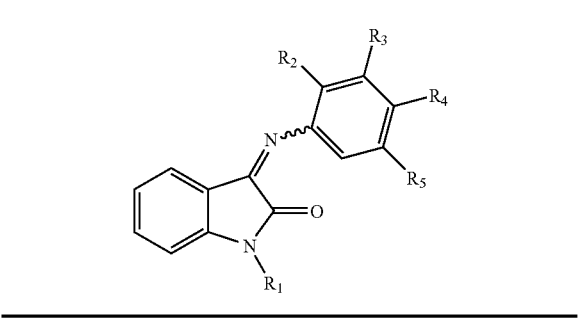
| 34 | 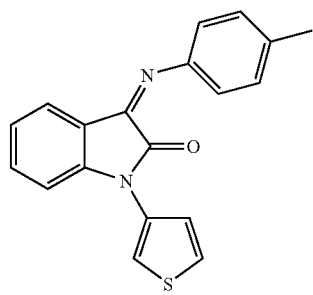 |
| 35 | 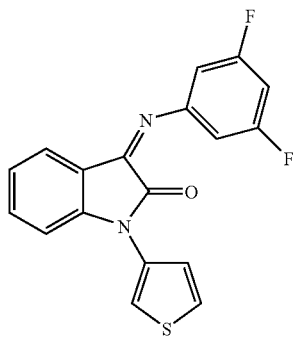 |
| 36 | 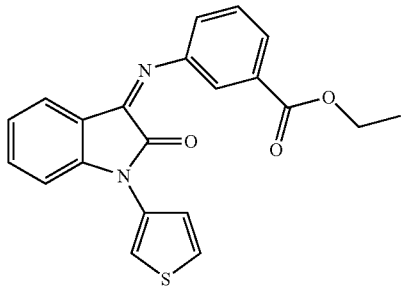 |
| 37 | 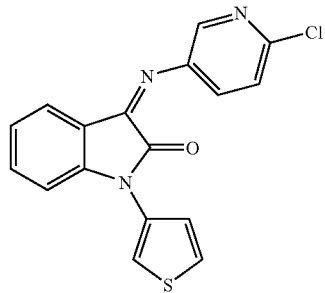 |
TABLE 1-continued
Chemical Structures of Compounds
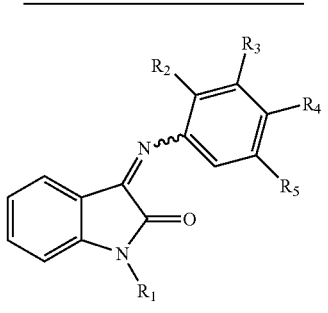
| 38 | 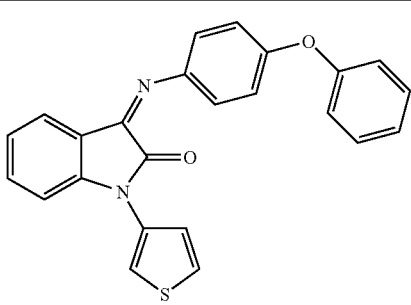 |
| 39 | 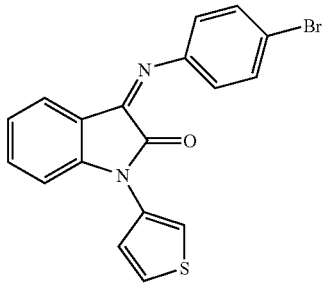 |
| 40 | 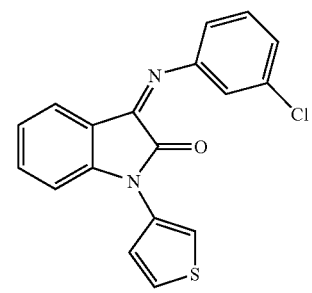 |
| 41 | 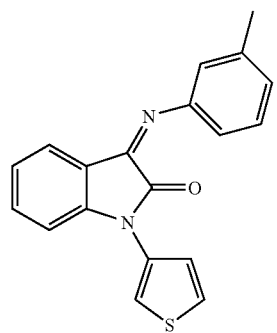 |

TABLE 1-continued
Chemical Structures of Compounds
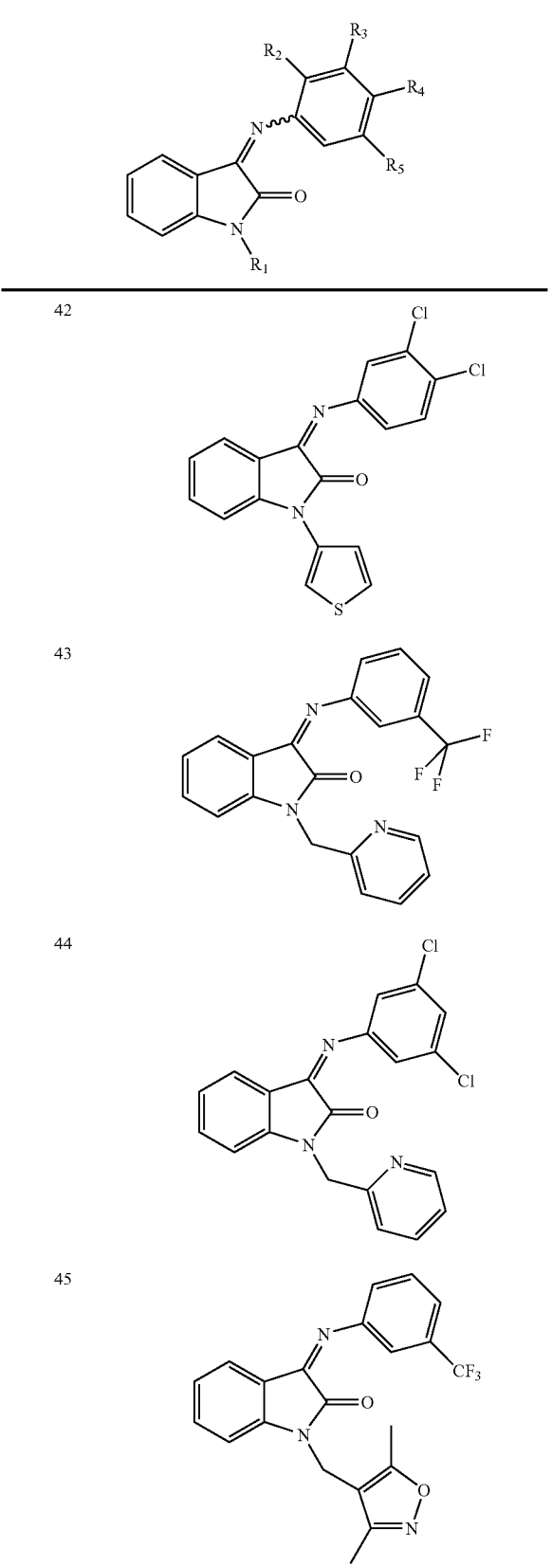
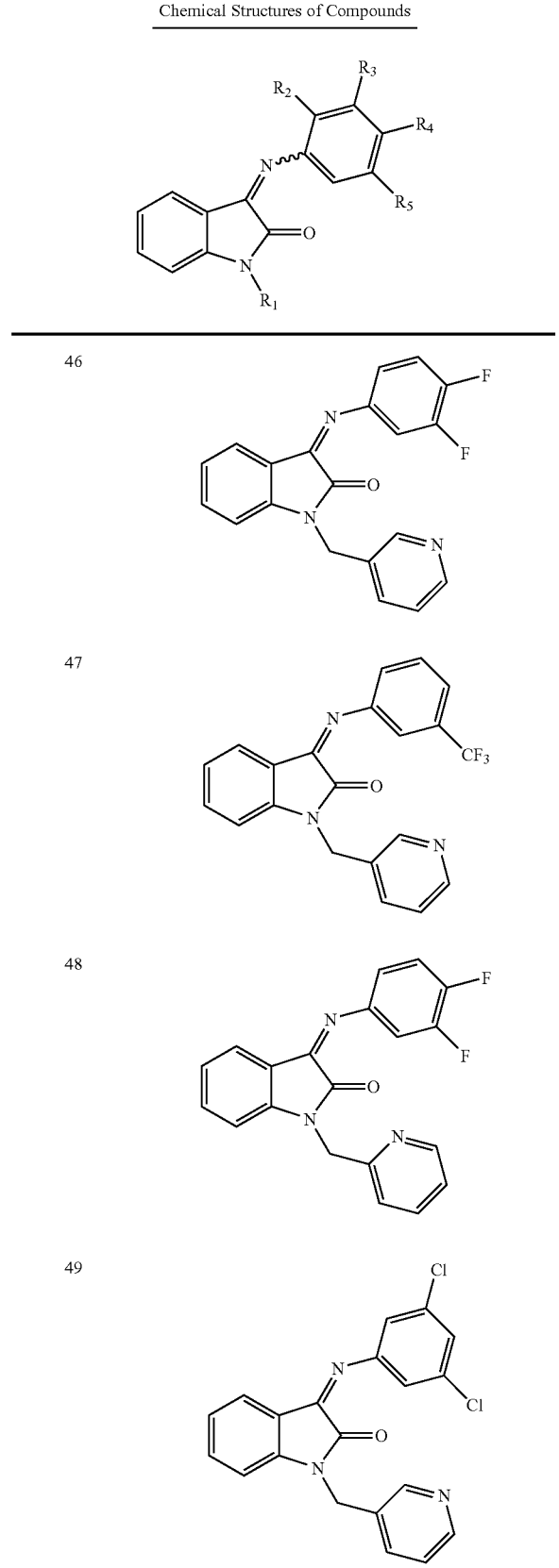

TABLE 1-continued
Chemical Structures of Compounds
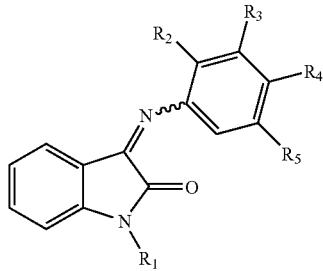
| 50 | 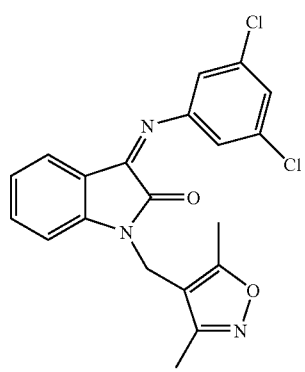 |
| --- | --- |
| 51 | 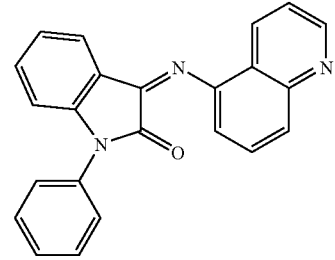 |
| 52 | 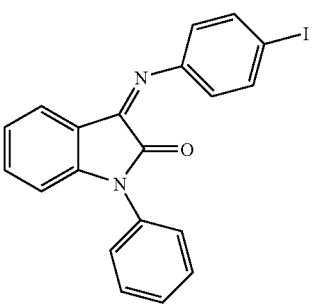 |
| 53 | 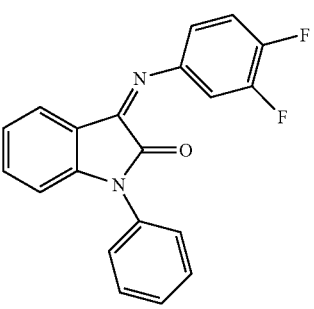 |
TABLE 1-continued
Chemical Structures of Compounds
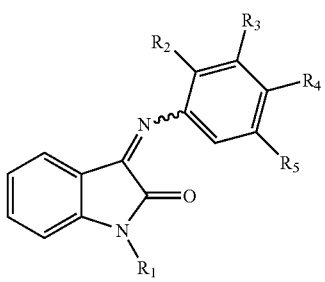
| 54 | 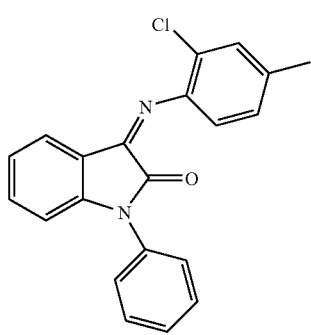 |
| --- | --- |
| 55 | 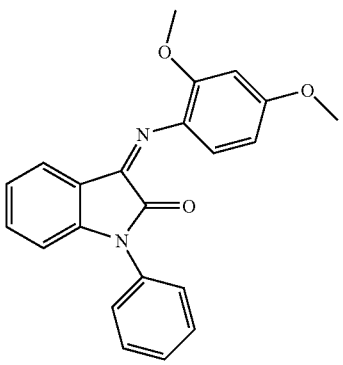 |
| 56 | 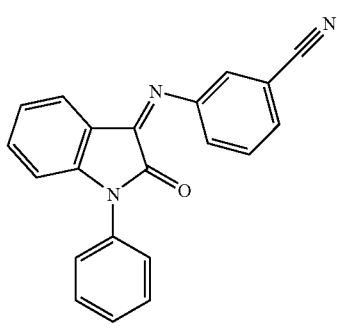 |

TABLE 1-continued
Chemical Structures of Compounds
| | |
|---|---|
| 57 | 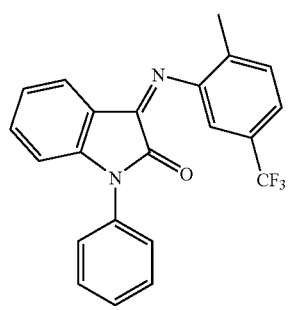 |
| 58 | 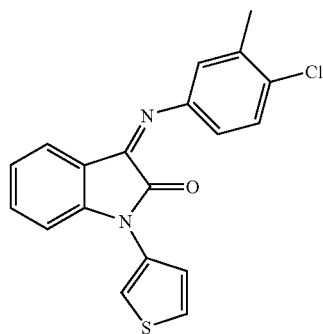 |
| 59 | 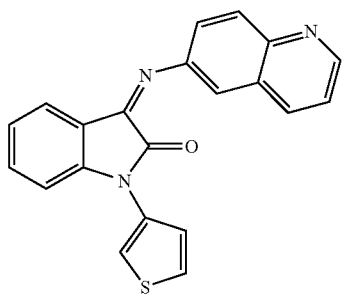 |
| 60 | 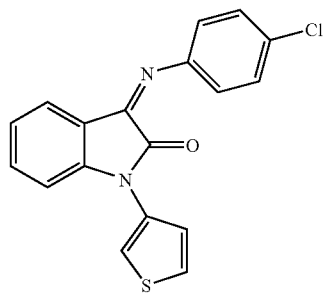 |
TABLE 1-continued
Chemical Structures of Compounds
| | |
|---|---|
| 61 | 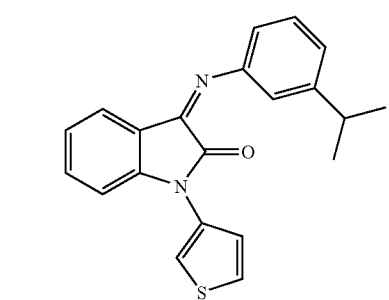 |
| 62 | 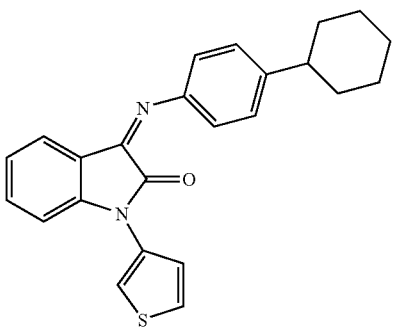 |
| 63 | 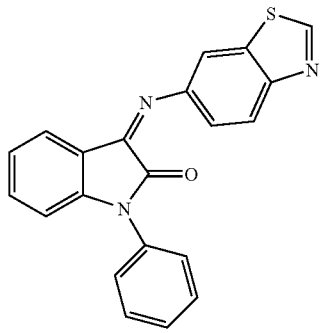 |
| 64 | 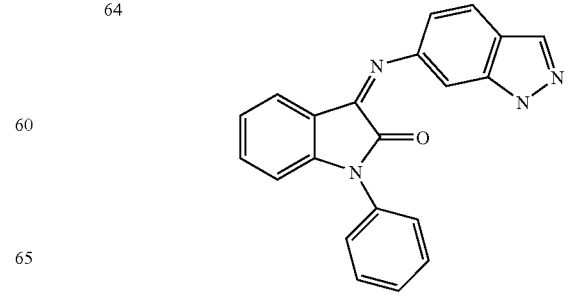 |

TABLE 1-continued
Chemical Structures of Compounds
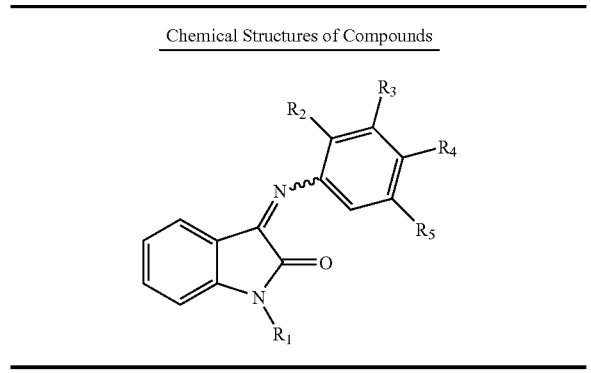
| 65 | 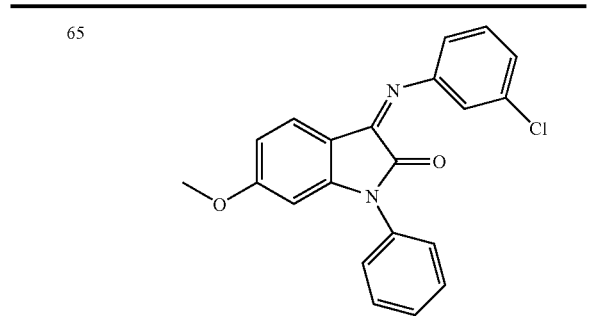 |
| 66 | 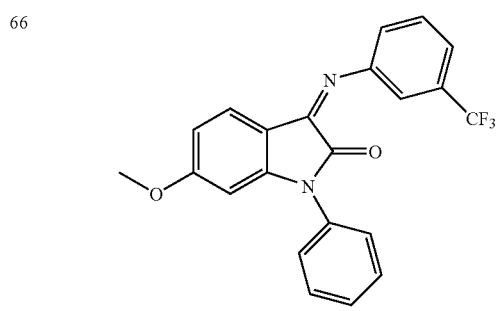 |
| 67 | 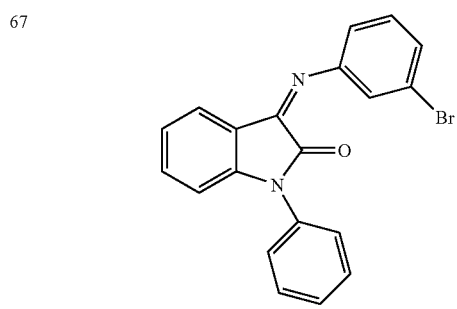 |
| 68 | 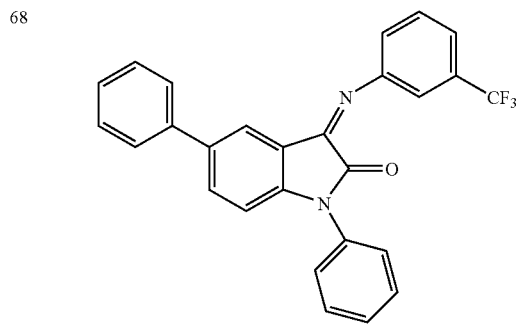 |
TABLE 1-continued
Chemical Structures of Compounds
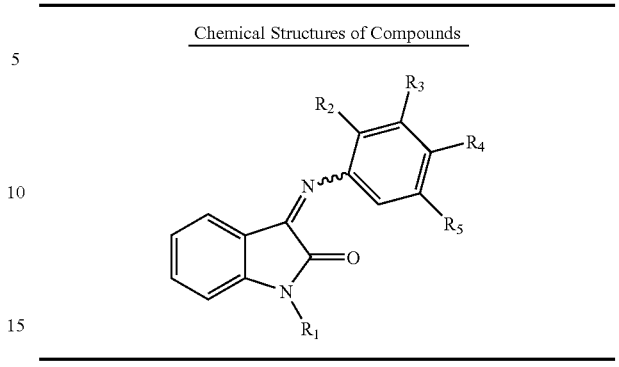
| 69 | 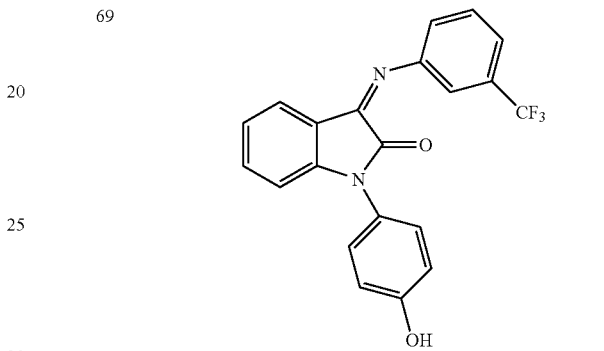 |
| 70 | 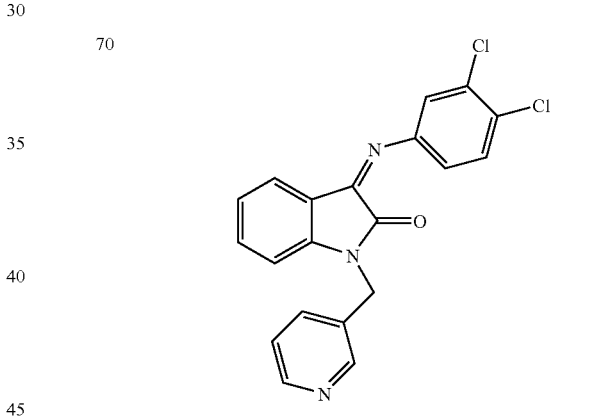 |
Key: Ph = Phenyl  OMe = Methoxy  OEt = Ethoxy  Me = Methyl  OPh = Phenoxy
Scheme 1<sup>a</sup>
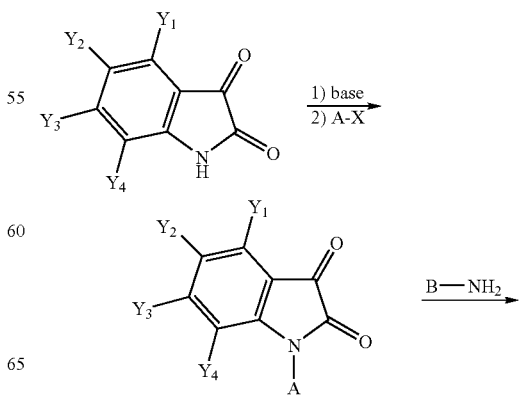

-continued

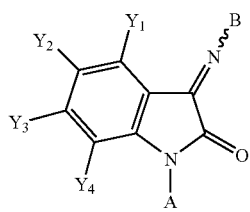

Scheme 2ª

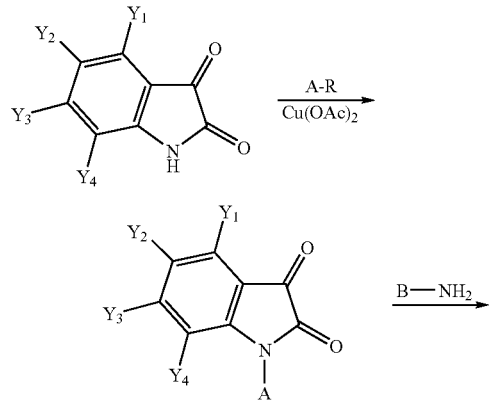

ªY$_1$, Y$_2$, Y$_3$, Y$_4$, A and B are defined as described in the specification. X is a leaving group such as Cl, Br, I, or OTs. R is a boric acid or dialkylborate group.

Scheme 3ª. Synthesis of Isatins

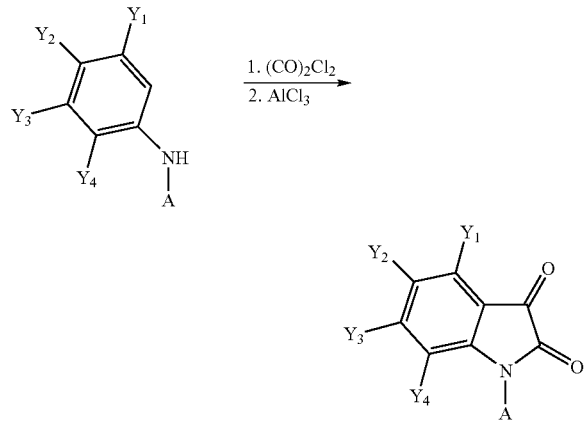

ªY$_1$, Y$_2$, Y$_3$, Y$_4$ and A are defined as described in the specification.

Scheme 4ª. Synthesis of Substituted Iminoindolones

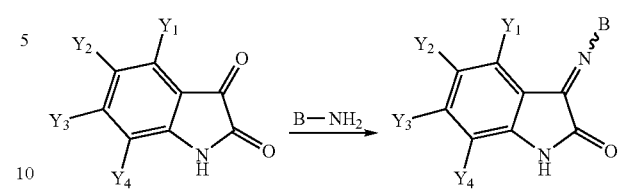

ªY$_1$, Y$_2$, Y$_3$, Y$_4$, A, and B are defined as described in the specification. X is a leaving group such as Cl, Br, I, or OTs. R is a boric acid or dialkylborate group.

Scheme 5ª. Synthesis of Aryl or Heteroaryl-Substituted Iminoindolones

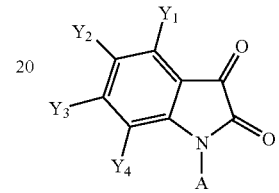

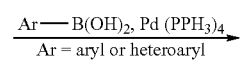

ªA and B are defined as described in the specificaton.

Pharmaceutical Compositions

As a specific embodiment of an oral composition of a compound of this invention, 100 mg of one of the compounds described herein is formulated with sufficient finely divided lactose to provide a total amount of 580 to 590 mg to fill a size O hard gel capsule.

The indolone compounds can be administered by any known means. For example, the compounds may be formulated as a capsule, suppository, cream, inhalant, or transdermal patch. Compositions suitable for oral administration include solid forms, such as pills, capsules, granules, tablets, and powders, and liquid forms, such as solutions, syrups, elixirs, and suspensions. Forms useful for parenteral administration include sterile solutions, emulsions, and suspensions.

Optimal dosages to be administered may be determined by those skilled in the art, and will vary with the particular compound in use, the strength of the preparation, the mode of administration, and the advancement of the disease condition. Additional factors depending on the particular subject being treated will result in a need to adjust dosages, including subject age, weight, gender, diet, and time of administration. In the subject application a "therapeutically effective amount" is any amount of a compound which, when administered to a subject suffering from a disease against which the compounds are effective, causes reduction, remission, or regression of the disease. In the present application, a "subject" is a vertebrate, a mammal or a human.

Experimental Details
II. In-Vivo Model

A. Materials and Methods

Effects of Compound 2 on Cognition

This study was undertaken to demonstrate that the cognitive task such as contextual memory and object recognition memory in mice is enhanced by treatment with Compound 2.

Contextual Memory. Contextual memory is a form of Pavlovian fear conditioning in which a naïve mouse is placed into a novel chamber (context) containing distinct visual, olfactory and tactile cues. After a few seconds of acclimation, the mouse receives a brief, mild electric shock to its feet. From this negative experience, the mouse will remember for months that that chamber is dangerous. When placed back into the same context at some later time after training, the mouse's natural response to danger is to "freeze," sitting stone still for many seconds. This is similar to what happens to humans when they experience fear. The percent of time during an observation period that the mouse spends frozen represents a quantitative measure (memory score) of its memory of the context.

Contextual conditioning has been extensively used to investigate the neural substrates mediating fear-motivated learning (Phillips, R. G., and LeDoux, J. E. 1992; Kim et al. 1993; Bourtchouladze et al. 1994; 1998). Contextual conditioning has been also used to study the impact of various mutations on hippocampus-dependent memory (Bourtchouladze et al. 1994; 1998; Silva A. J. et al. 1996; Kogan J. L. et al. 1996; Abel, T. et al. 1997; Giese K. P., et al. 1998) and strain and genetic background differences in mice (Logue et al. 1996; Chen et al 1996; Nguyen, P. V. 2000). Because robust memory can be triggered with a few minutes training session, contextual conditioning has been especially useful to study biology of temporally distinct processes of short- and long-term memory (Kim et al. 1993; Bourtchouladze et al. 1994; 1998; Abel, T. et al. 1997). As such, contextual conditioning is an excellent model to evaluate the role of various novel drug-compounds in hippocampus-dependent memory.

Object Recognition. Object recognition is an ethnologically relevant task for rodents, which does not result from negative reinforcement (foot shock). This task relies on the natural curiosity of rodents to explore novel objects in their environments more than familiar ones. Obviously, for an object to be "familiar," the animal must have attended to it before and remembered that experience. Hence, animals with better memory will attend and explore a new object more than a familiar one.

During training, a mouse is presented with two identical, novel objects. Mice explore them equally by approaching, sniffing and crawling over them. During testing, the animal is presented with the training object and a second, novel one. Memory of the training object renders it familiar to the animal, and it then spends more time exploring the new novel object rather than the familiar one (Bourtchouladze t al., 2003). Recent neuroimaging studies in humans demonstrated that memory in object recognition depends on prefrontal cortex (PFC) (Smith, 1999; Deibert, 1999). Consistent with these findings, rats with the PFC lesions show poor working memory when they are required to discriminate between familiar and novel objects (Mitchell, 1998). Other studies on monkeys and rodents suggest that the hippocampus is important for novel object recognition (Teng, 2000; Mumby, 2001). Hence, object recognition provides an excellent behavioral model to evaluate drug-compound effects on cognitive task associated with function of hippocampus and cortex.

Methods

Subjects. Young-adult (10-12 weeks old) C57Bl/6 male mice (Taconic, N.Y.) were used. The mice were housed (5 mice) in standard laboratory cages and maintained on a 12:12 light-dark cycle. The experiments were always conducted during the light phase of the cycle. The day before the initiation of the experiment, mice were housed single in individual cages and maintained so until the end of the experiment. With the exception of testing times, the mice had liberal access to food and water. The experiments were conducted in accordance with Animal Welfare Assurance #A3280-01. Animals were maintained in accordance with the Animal Welfare Act and Department of Health and Human Services Guide.

Contextual Conditioning Training and Testing. To assess contextual memory, a standardized contextual fear conditioning task originally developed for evaluation of memory in cyclic AMP response element binding protein ("CREB") knock-out mice was used (Bourtchouladze et al., 1994). On the training day, the mouse was placed into the conditioning chamber (Med Associates, Inc., VA) for 2 minutes before the onset of unconditioned stimulus (US), 0.5 mA, of 2 second foot shock. The US was repeated two times with a 1 min inter-trial interval between shocks. Training was performed by automated software package (Med Associates, Inc., VA). After the last training trial, the mice were left in the conditioning chamber for another 30 seconds and were then placed back in their home cages. 24 hours after training, the mouse was placed into the same training chamber and contextual memory was assessed by scoring freezing behavior ('freezing' serves as memory score). Freezing was defined as the complete lack of movement in intervals of 5 seconds (Kim et al., 1993; Phillips & LeDoux, 1992; Bourtchouladze et al., 1994; 1998; Abel et al., 1997). Total testing time lasted 3 minutes. After each experimental subject, the experimental apparatus was thoroughly cleaned with 75% ethanol, water, dried, and ventilated for a few minutes.

Contextual Conditioning Data Analysis. All experiments were designed and performed in a balanced fashion, meaning that (i) for each experimental condition (e.g. a specific dose-effect) we used an equal number of experimental and control mice; (ii) each experimental condition was replicated 2-3 independent times, and replicate days were added to generate final number of subjects. The proceeding of each experiment was filmed. In each experiment, the experimenter was unaware (blind) to the treatment of the subjects during training and testing. Data were analyzed by Student's unpaired t test using a software package (Statwiew 5.0.1; SAS Institute, Inc). All values in the text and figures are expressed as mean±SEM.

Object Recognition Training and Testing. Animals were handled for 3-5 minutes for 5 days. The day before training, an individual animal was placed into a training apparatus (a Plexiglas box of L=48 cm; W=38 cm and H=20 cm) located in a dimly lit room and allowed to habituate to the environment for 15 minutes (Bourtchouladze et al., 2003). Training was initiated 24 hours after habituation. A mouse was placed back into the training box, which contained two identical objects (e.g. a small cone-shaped object), and was allowed to explore these objects. The objects were placed into the central area of the box and the spatial position of objects (left-right sides) was counterbalanced between subjects. Animals were trained for 15 minutes.

To test for memory retention, mice were observed for 10 minutes, 24 hours after training. A mouse was presented with two objects, one of which was used during training, and thus was 'familiar' and the other of which was novel (e.g. a small pyramid-shape object). To insure that the discrimination targets do not differ in smell, after each experimental subject, the apparatus and the objects were thoroughly cleaned with 90% ethanol, dried and ventilated for a few minutes.

Object Recognition Data Analysis. The experiments were videotaped via an overhead video camera system. Types were reviewed by a blinded observer and the following behavioral parameters were determined: time of exploration of an each object; the total time of exploration of the objects; number of approaches to the objects; and time (latency) to first approach to an object. The discrimination index—memory score—was determined as described previously (Ennaceur et al., 1997, Bourtchouladze et al., 2003). These data were analyzed by Student's unpaired t test using a software package (Statwiew 5.0.1; SAS Institute, Inc). All values in the text and figures are expressed as mean±SEM.

Drug Compound Administration. Compound 2 was freshly prepared from a stock solution (10 mg/ml DMSO), which was maintained at 4° C. Compound 2 was dissolved in a suspension of 5% DMSO and 95% CMC at 2% in water and administered intraperitonially (I.P.) at doses 5 mg/kg; 10 mg/kg and 30 mg/kg 20 min before training or at 1 mg/kg and 30 mg/kg orally 60 min before training. Control animals received vehicle alone (5% DMSO and 95% CMC at 2% in water). For each training and drug-injecting procedure, an experimentally naïve group of animals was used.

Results

Contextual Memory. To evaluate the effects of Compound 2 on contextual memory, mice were injected with Compound 2 or vehicle 20 minutes before training and trained with 2 training trials (US). Mice were then tested in the same context 24 hours after training (See FIG. 1). I.P. administration of 5 mg/kg, 10 mg/kg and 30 mg/kg of Compound 2 significantly facilitated freezing to context 24 hr after training (40.3±4.7% vs. 24.5±3.2% for 5 mg/kg Compound 2 (n=6) vs. controls (n=6), p<0.05; 51.4±9.1% vs. 24.5±3.2% for 10 mg/kg Compound 2 (n=6) vs. controls (n=6), p<0.01; and 49.1±3.7% vs. 24.5±3.2% for 30 mg/kg Compound 2 (n=6) vs. controls (n=6), p<0.001; Student's unpaired t test).

Figure 2:
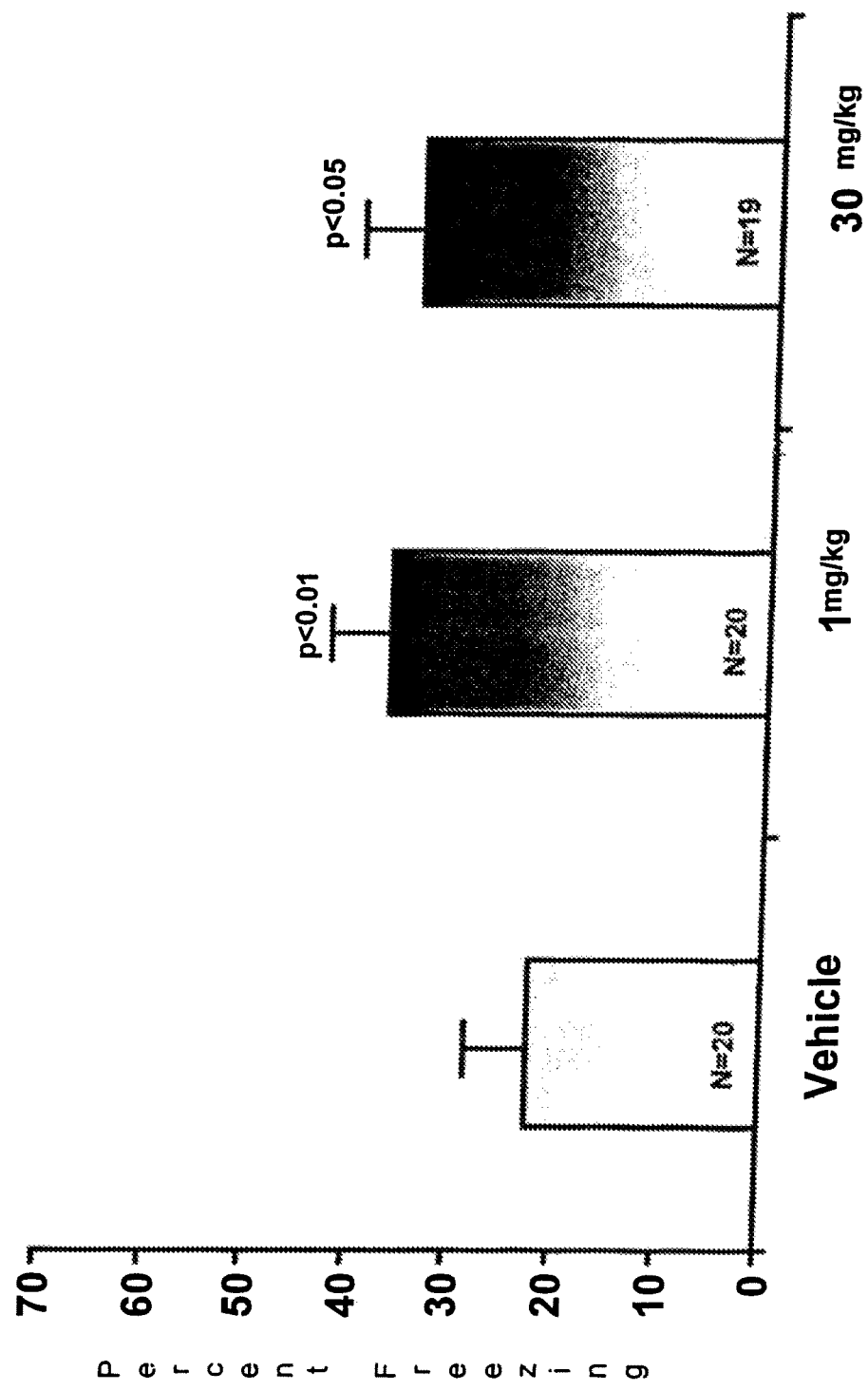
FIG. 2: Effects of Compound 2 on contextual memory in mice. A single dose of 1 mg/kg or 30 mg/kg of Compound 2 significantly enhanced 24 hr contextual memory in mice. All dosages of vehicle and Compound 2 were administered orally.

Similarly, oral delivery of 1 mg/kg and 30 mg/kg of Compound 2 sixty (60) min before training significantly facilitated 24 h contextual memory (36.4±3.9% vs. 22.3±3.2%, for 1 mg/kg Compound 2 (n=20) vs. controls (n=20), p<0.01; and 34.1±4.3% vs. 22.3±3.2% for 30 mg/kg Compound 2 (n=19) vs. controls (n=20), p<0.05; Student's unpaired t test; (See FIG. 2).

Figure 3:
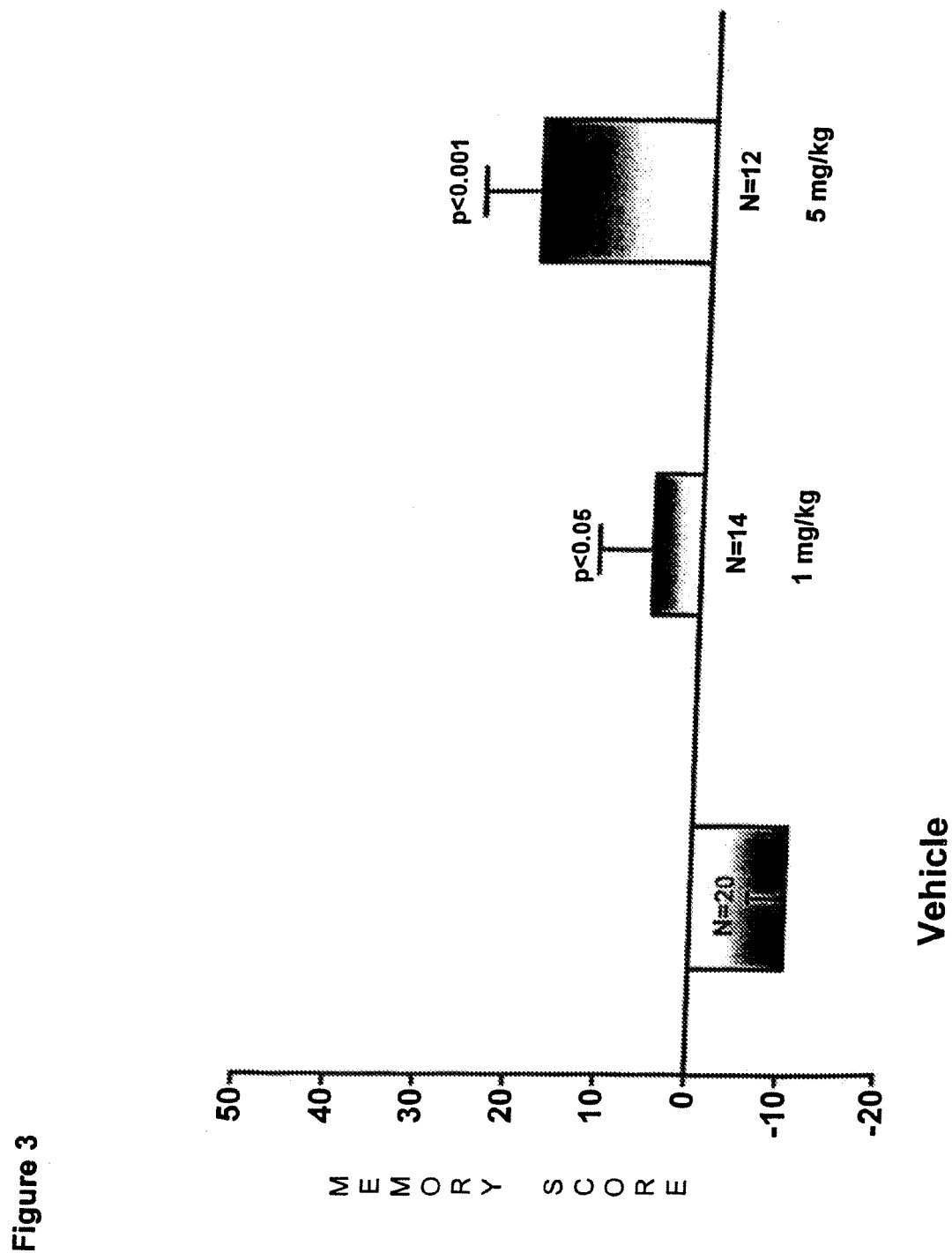
FIG. 3: Effects of Compound 2 on contextual memory in mice. Injections of 1 mg/kg and 5 mg/kg of Compound 2 twenty (20) minutes before training ameliorated long-term memory deficit in C57BL/6 mice. All dosages of vehicle and Compound 2 were administered intraperitonially (i.p.).

Object Recognition. To evaluate the effects of Compound 2 on object recognition, compound or vehicle alone was administered i.p. to C57BL/6 mice 20 minutes before a 15-minute training session. Vehicle-injected C57BL/6 mice showed poor 24 hour object recognition. However, a single administration of 1 mg/kg Compound 2 (n=14) or 5 mg/kg Compound 2 (n=12) significantly enhanced recognition memory [Discrimination Index (DI)=−10.2±4 vs. 5.1±6 for vehicle-vs. 1 mg/kg Compound 2 injected mice; p<0.05; and DI=−10.2±4 vs. 18.8±6.6 for vehicle-vs. 5 mg/kg Compound 2 injected mice; p<0.0005] (See FIG. 3).

The results of the aforementioned experiments demonstrate that a therapeutically effective amount of the indolone compound(s) described herein is useful to treat a subject suffering from a cognitive impairment or a cognitive disorder.

REFERENCES

Abel, T., et al., (1997). Genetic demonstration of a role for PKA in the late phase of LTP and in hippocampus-based long-term memory. *Cell* 88: 615-626.

American Psychiatric Association. *Diagnostic and statistical manual of mental disorders* (DSM-IV), APA, Washington, D.C., 1994. *Asymmetric Synthesis* (1983) Vol: 2-5, Academic Press, Editor Morrison, J.

Bourtchouladze, R., et al., (1998). Different training procedures recruit either one or two critical periods for contextual memory consolidation, each of which requires protein synthesis and PKA. *Learn Mem* 5: 365-374.

Bourtchouladze, R., et al., (2003). A mouse model of Rubinstein-Taybi syndrome: defective long-term memory is ameliorated by inhibitors of phosphodiesterase 4. *Proc Natl Acad Sci USA* 100: 10518-10522.

Bourtchouladze, R., et al., (1994). Deficient long-term memory in mice with a targeted mutation of the cAMP-responsive element-binding protein. *Cell* 79: 59-68.

Bryant, W. M. III, et al., (1993) *Synthetic Communications*, 23: 1617-1625.

Coppola, G. M. (1987) *Journal of Heterocyclic Chemistry*, 24: 1249.

Deibert, E., et al., (1999). Neural pathways in tactile object recognition. *Neurology* 52: 1413-1417.

Ennaceur, A., and Aggleton, J. P. (1997). The effects of neurotoxic lesions of the perirhinal cortex combined to fornix transection on object recognition memory in the rat. *Behav Brain Res* 88: 181-193.

Garden, S. J., et al., (1998). *Synthetic Communications*, 28: 1679-1689.

Giese, K. P., et al., (1998). Autophosphorylation at Thr286 of the alpha calcium-calmodulin kinase II in LTP and learning. *Science* 279: 870-873.

Green, T. W. and Wuts, P. G. M. (1991) *Protection Groups in Organic Synthesis*, second Edition John Wiley & Sons, New York.

Hess, B. A. Jr. and Corbino, S. (1971) *Journal of Heterocyclic Chemistry*, 8: 161.

Jaques, J., et al., (1981) *Enantiomers, Racemates and Resolutions*. John Wiley & Sons.

Kim, J. J., et al., (1995). Hippocampectomy impairs the memory of recently, but not remotely, acquired trace eyeblink conditioned responses. *Behav Neurosci* 109: 195-203.

Kim, J. J., et al., (1993). Effects of amygdala, hippocampus, and periaqueductal gray lesions on short- and long-term contextual fear. *Behav Neurosci* 107: 1093-1098.

Kogan, J. H., et al., (1997). Spaced training induces normal long-term memory in CREB mutant mice. *Curr Biol* 7: 1-11.

Logue, S. F., Paylor, R., and Wehner, J. M. (1997). Hippocampal lesions cause learning deficits in inbred mice in the Morris water maze and conditioned-fear task. *Behav Neurosci* 111: 104-113.

Mitchell, J. B., and Laiacona, J. (1998). The medial frontal cortex and temporal memory: tests using spontaneous exploratory behaviour in the rat. *Behav Brain Res* 97: 107-113.

Mumby, D. G. (2001). Perspectives on object-recognition memory following hippocampal damage: lessons from studies in rats. *Behav Brain Res* 127: 159-181.

Nguyen, P. V., et al., (2000). Strain-dependent differences in LTP and hippocampus-dependent memory in inbred mice. *Learn Mem* 7: 170-179.

Nógrádi, M. (1987) *Stereoselective Synthesis*, VCH, Editor Ebel, H.

Otsuka, S. and Kobayashi, Y. (1964) A radioisotopic assay for monoamine oxidase determinations in human plasma. *Biochem. Pharmacol.*, 13: 995-1006.

Phillips, R. G., and LeDoux, J. E. (1992). Differential contribution of amygdala and hippocampus to cued and contextual fear conditioning. *Behav Neurosci* 106: 274-285.

Pittenger, C., Huang, et al., (2002). Reversible inhibition of CREB/ATF transcription factors in region CA1 of the dorsal hippocampus disrupts hippocampus-dependent spatial memory. *Neuron* 34: 447-462.

Silva, A. J., et al., (1996). Impaired learning in mice with abnormal short-lived plasticity. *Curr Biol* 6: 1509-1518.

Teng, E., et al., (2000). Contrasting effects on discrimination learning after hippocampal lesions and conjoint hippocampal-caudate lesions in monkeys. *J Neurosci* 20: 3853-3863.

Weiss, J. M., et al., (1998) *Annals of the N.Y. Acad. Sci.*, (Ed. T. Hökfelt, Tamas Bartfai and J. Crawley) p. 364-382.

What is claimed:

1. A method of treating a subject suffering from a memory impairment comprising administering to the subject an amount of a compound effective to enhance the subject's memory, wherein the compound has the structure:

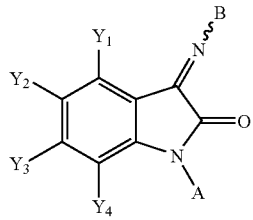

wherein each of $Y_1$, $Y_2$, $Y_3$, and $Y_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, or $C_5$-$C_7$ cycloalkenyl; —F, —Cl, —Br, or —I; —$NO_2$; —$N_3$; —CN; —$OR_4$, —$SR_4$, —$OCOR_4$, —$COR_4$, —$NCOR_4$, —$N(R_4)_2$, —$CON(R_4)_2$, or —$COOR_4$; aryl or heteroaryl; or any two of $Y_1$, $Y_2$, $Y_3$, and $Y_4$ present on adjacent carbon atoms can constitute a methylenedioxy group;

wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl;

wherein A is A', straight chained or branched $C_1$-$C_7$ alkyl, aryl, heteroaryl, aryl($C_1$-$C_6$)alkyl or heteroaryl($C_1$-$C_6$) alkyl;

wherein A' is

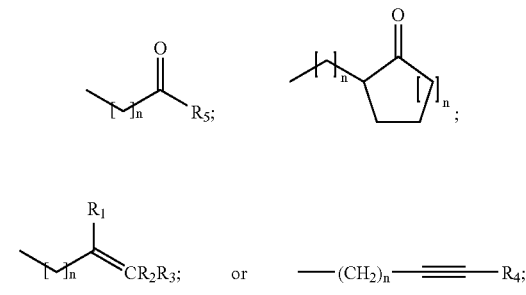

wherein $R_1$ and $R_2$ are each independently —H, straight chained or branched $C_1$-$C_7$ alkyl, —F, —Cl, —Br, —I, —$NO_2$, or —CN;

wherein $R_3$ is —H, straight chained or branched $C_1$-$C_7$ alkyl, —F, —Cl, —Br, —I, —$NO_2$, —CN, —$OR_6$ aryl or heteroaryl;

wherein $R_5$, is straight chained or branched $C_1$-$C_7$ alkyl, —$N(R_4)_2$—, $OR_6$, or aryl;

wherein $R_6$ is straight chained or branched $C_1$-$C_7$ alkyl or aryl; wherein B is aryl, or heteroaryl; provided however, if B is aryl or heteroaryl the carbon atom or carbon atoms ortho to the nitrogen atom of the imine bond may only be substituted with one or more of the following: —H, —F, —Cl, —Br, —I, —CN, methyl, ethyl or methoxy;

wherein each n is independently an integer from 1 to 4 inclusive; wherein the compound is a pure Z imine isomer, a pure E imine isomer, or a mixture of Z and E imine isomers;

or a pharmaceutically acceptable salt thereof.

2. The method of claim 1, wherein the compound is enantiomerically and diastereomerically pure.

3. The method of claim 1, wherein the compound is enantiomerically or diastereomerically pure.

4. The method of claim 1, wherein the compound is a pure Z imine isomer.

5. The method of claim 1, wherein the compound is a pure E imine isomer.

6. The method of claim 1, wherein the compound is a mixture of Z and E imine isomers.

7. The method of claim 1, wherein the compound has the structure:

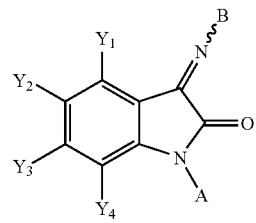

wherein each of $Y_1$, $Y_2$, $Y_3$, and $Y_4$ is independently —H; straight chained or branched $C_1$-$C_7$ alkyl, —$CF_3$, —F, —Cl, —Br, —I, —$OR_4$, —$N(R_4)_2$, or —$CON(R_5)_2$;

wherein each $R_4$ independently H, straight chained or branched $C_1$-$C_7$ alkyl, —$CF_3$, or phenyl;

wherein A is A', straight chained or branched $C_1$-$C_7$ alkyl, aryl, heteroaryl, aryl($C_1$-$C_6$)alkyl or heteroaryl($C_1$-$C_6$)alkyl; and wherein A' is

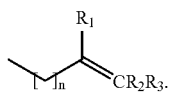

8. The method of claim 7, wherein B is aryl.

9. The method of claim 8, wherein B is phenyl and the phenyl is optionally substituted with one or more of the following: —H; —F, —Cl, —Br, —$CF_3$, straight chained or branched $C_1$-$C_7$ alkyl, —$N(R_4)_2$, —$OR_4$, —$COR_4$, —$NCOR_4$, —$CO_2R_4$, or —$CON(R_4)_2$.

10. The method of claim 9, wherein A is aryl.

11. The method of claim 9, wherein A is heteroaryl.

12. A method of treating a subject suffering from a memory impairment comprising administering to the subject an amount of a compound effective to enhance the subject's memory, wherein the compound has the structure:

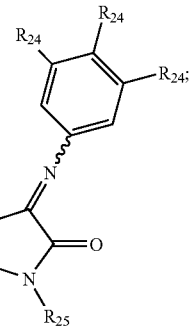

wherein each $R_{24}$ is independently one or more of the following: H, F, Cl, Br, I, $CF_3$ or $OCH_3$;

wherein $R_{25}$ is methyl, ethyl, allyl, or phenyl and the phenyl is optionally substituted with F, Cl, Br, $CF_3$, or $OR_4$, and wherein each $R_4$ is independently —H; straight chained or branched $C_1$-$C_7$ alkyl, monofluoroalkyl or polyfluoroalkyl; straight chained or branched $C_2$-$C_7$ alkenyl or alkynyl; $C_3$-$C_7$ cycloalkyl, $C_5$-$C_7$ cycloalkenyl, aryl or aryl($C_1$-$C_6$)alkyl.

* * * * *